United States Patent
Cowan et al.

(10) Patent No.: US 11,998,752 B2
(45) Date of Patent: *Jun. 4, 2024

(54) WEARABLE CARDIOVERTER DEFIBRILLATOR WITH A NON-INVASIVE BLOOD PRESSURE MONITOR

(71) Applicant: West Affum Holdings DAC, Dublin (IE)

(72) Inventors: Kenneth F. Cowan, Everett, WA (US); Steven E. Sjoquist, Lynnwood, WA (US); Zoie R. Engman, Kirkland, WA (US); Erick M. Roane, Bellevue, WA (US); Laura M. Gustavson, Redmond, WA (US); Douglas K. Medema, Everett, WA (US); Garrett M. Kotlarchik, Kenmore, WA (US); Pamela Breske, Newcastle, WA (US); Jonathan P. Niegowski, Issaquah, WA (US); Joseph L. Sullivan, Kirkland, WA (US); Robert R. Buchanan, Bothell, WA (US)

(73) Assignee: West Affum Holdings DAC, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 17/720,146

(22) Filed: Apr. 13, 2022

(65) Prior Publication Data

US 2022/0241601 A1 Aug. 4, 2022

Related U.S. Application Data

(63) Continuation of application No. 16/394,618, filed on Apr. 25, 2019, now Pat. No. 11,331,508.

(Continued)

(51) Int. Cl.
*A61B 5/00* (2006.01)
*A61B 5/01* (2006.01)
(Continued)

(52) U.S. Cl.
CPC .......... *A61N 1/3987* (2013.01); *A61B 5/0004* (2013.01); *A61B 5/01* (2013.01);
(Continued)

(58) Field of Classification Search
CPC .. A61N 1/3987; A61N 1/3904; A61N 1/3925; A61N 1/3968; A61B 5/0004;
(Continued)

(56) References Cited

U.S. PATENT DOCUMENTS

| 3,724,455 A | 4/1973 | Unger |
| 4,583,524 A | 4/1986 | Hutchins |

(Continued)

FOREIGN PATENT DOCUMENTS

WO 9839061 A2 9/1998

OTHER PUBLICATIONS

"Long Term Blood Pressure Measurement and More" by SOMNOmedics GmbH, 2000-2014.
(Continued)

*Primary Examiner* — Scott M. Getzow
(74) *Attorney, Agent, or Firm* — Spectrum IP Law Group LLC

(57) ABSTRACT

A wearable cardioverter defibrillator (WCD) system comprises a plurality of patient parameter electrodes and a plurality of defibrillator electrodes to contact a patient's skin when the WCD is delivering therapy to the patient, a processor to receive one or more patient parameters from the one or more patient parameter electrodes, an energy storage device to store a charge to provide electrical therapy to the patient via the plurality of defibrillator electrodes, and a
(Continued)

SAMPLE COMPONENTS OF WEARABLE CARDIOVERTER DEFIBRILLATOR (WCD) SYSTEM non-invasive blood pressure (NIBP) monitor to obtain a blood pressure measurement of the patient and to provide the blood pressure measurement to the processor. The processor is to determine whether to provide electrical therapy to the patient based on the one or more patient parameters during an episode, and to obtain the blood pressure measurement from the NIBP monitor during the episode.

19 Claims, 8 Drawing Sheets

Related U.S. Application Data

(60) Provisional application No. 62/662,717, filed on Apr. 25, 2018.

(51) Int. Cl.
| | | |
|---|---|---|
| *A61B 5/0205* | (2006.01) | |
| *A61B 5/1455* | (2006.01) | |
| *A61B 5/282* | (2021.01) | |
| *A61B 5/361* | (2021.01) | |
| *A61B 5/363* | (2021.01) | |
| *A61B 5/366* | (2021.01) | |
| *A61N 1/39* | (2006.01) | |
| *A61B 5/021* | (2006.01) | |
| *A61B 5/024* | (2006.01) | |
| *A61B 5/08* | (2006.01) | |

(52) U.S. Cl.
CPC ...... *A61B 5/02055* (2013.01); *A61B 5/14552* (2013.01); *A61B 5/282* (2021.01); *A61B 5/361* (2021.01); *A61B 5/363* (2021.01); *A61B 5/366* (2021.01); *A61B 5/6805* (2013.01); *A61N 1/3904* (2017.08); *A61N 1/3925* (2013.01); *A61N 1/3968* (2013.01); *A61B 5/021* (2013.01); *A61B 5/024* (2013.01); *A61B 5/0809* (2013.01); *A61B 5/6824* (2013.01); *A61B 5/6828* (2013.01); *A61B 5/6829* (2013.01); *A61B 2562/0271* (2013.01)

(58) Field of Classification Search
CPC ... A61B 5/01; A61B 5/02055; A61B 5/14552; A61B 5/282; A61B 5/361; A61B 5/363; A61B 5/366; A61B 5/6805; A61B 5/021; A61B 5/024; A61B 5/0809; A61B 5/6824; A61B 5/6828; A61B 5/6829; A61B 2562/0271; A61B 5/0205; A61B 5/02108; A61B 5/4836
See application file for complete search history.

(56) References Cited

U.S. PATENT DOCUMENTS

| | | | |
|---|---|---|---|
| 4,619,265 A | 10/1986 | Morgan et al. | |
| 4,928,690 A | 5/1990 | Heilman et al. | |
| 4,955,381 A | 9/1990 | Way et al. | |
| 5,078,134 A | 1/1992 | Heilman et al. | |
| 5,228,449 A | 7/1993 | Christ et al. | |
| 5,348,008 A | 9/1994 | Bornn et al. | |
| 5,353,793 A | 10/1994 | Bornn | |
| RE34,800 E | 11/1994 | Hutchins | |
| 5,394,892 A | 3/1995 | Kenny et al. | |
| 5,405,362 A | 4/1995 | Kramer et al. | |
| 5,474,574 A | 12/1995 | Payne et al. | |
| 5,662,690 A | 9/1997 | Cole et al. | |
| 5,782,878 A | 7/1998 | Morgan et al. | |
| 5,792,204 A | 8/1998 | Snell | |
| 5,902,249 A | 5/1999 | Lyster | |
| 5,913,685 A | 6/1999 | Hutchins | |
| 5,944,669 A | 8/1999 | Kaib | |
| 6,047,203 A | 4/2000 | Sackner et al. | |
| 6,065,154 A | 5/2000 | Hulings et al. | |
| 6,108,197 A | 8/2000 | Janik | |
| 6,148,233 A | 11/2000 | Owen et al. | |
| 6,201,992 B1 | 3/2001 | Freeman | |
| 6,263,238 B1 | 7/2001 | Brewer et al. | |
| 6,287,328 B1 | 9/2001 | Snyder et al. | |
| 6,304,780 B1 | 10/2001 | Owen et al. | |
| 6,319,011 B1 | 11/2001 | Motti et al. | |
| 6,334,070 B1 | 12/2001 | Nova et al. | |
| 6,356,785 B1 | 3/2002 | Snyder et al. | |
| 6,427,083 B1 | 7/2002 | Owen et al. | |
| 6,529,875 B1 | 3/2003 | Nakajima et al. | |
| 6,546,285 B1 | 4/2003 | Owen et al. | |
| 6,671,545 B2 | 12/2003 | Fincke | |
| 6,681,003 B2 | 1/2004 | Linder et al. | |
| 6,762,917 B1 | 7/2004 | Verbiest et al. | |
| 7,065,401 B2 | 6/2006 | Worden | |
| 7,559,902 B2 | 7/2009 | Ting et al. | |
| 7,865,238 B2 | 1/2011 | Brink | |
| 7,870,761 B2 | 1/2011 | Valentine et al. | |
| 7,974,689 B2 | 7/2011 | Volpe et al. | |
| 8,024,037 B2 | 9/2011 | Kumar | |
| 8,135,462 B2 | 3/2012 | Owen et al. | |
| 8,140,154 B2 | 3/2012 | Donnelly et al. | |
| 8,369,944 B2 | 2/2013 | Macho et al. | |
| 8,548,557 B2 | 10/2013 | Garstka et al. | |
| 8,615,295 B2 | 12/2013 | Savage et al. | |
| 8,644,925 B2 | 2/2014 | Volpe et al. | |
| 8,838,235 B2 | 9/2014 | Cowan et al. | |
| 8,897,860 B2 | 11/2014 | Volpe et al. | |
| 8,904,214 B2 | 12/2014 | Volpe et al. | |
| 8,965,500 B2 | 2/2015 | Macho et al. | |
| 9,008,801 B2 | 4/2015 | Kaib et al. | |
| 9,089,685 B2 | 7/2015 | Sullivan et al. | |
| 9,131,901 B2 | 9/2015 | Volpe et al. | |
| 9,132,267 B2 | 9/2015 | Kaib | |
| 9,408,548 B2 | 8/2016 | Volpe et al. | |
| 9,454,219 B2 | 9/2016 | Volpe et al. | |
| 9,592,403 B2 | 3/2017 | Sullivan | |
| 2002/0169584 A1 | 11/2002 | Fu et al. | |
| 2011/0022105 A9 | 1/2003 | Owen et al. | |
| 2003/0158593 A1 | 8/2003 | Heilman et al. | |
| 2005/0107833 A1 | 5/2005 | Freeman et al. | |
| 2005/0107834 A1 | 5/2005 | Freeman et al. | |
| 2008/0312542 A1* | 12/2008 | Banet ............... | A61B 5/02125 600/485 |
| 2008/0312709 A1 | 12/2008 | Volpe et al. | |
| 2009/0005827 A1 | 1/2009 | Weintraub et al. | |
| 2010/0007413 A1 | 1/2010 | Herleikson et al. | |
| 2010/0298899 A1* | 11/2010 | Donnelly ............. | A61N 1/3987 607/6 |
| 2011/0288604 A1 | 11/2011 | Kaib et al. | |
| 2011/0288605 A1 | 11/2011 | Kaib et al. | |
| 2012/0150008 A1 | 1/2012 | Lanar et al. | |
| 2012/0112903 A1 | 5/2012 | Kaib et al. | |
| 2012/0144551 A1 | 6/2012 | Guldalian | |
| 2012/0158075 A1 | 6/2012 | Kaib et al. | |
| 2012/0265265 A1 | 10/2012 | Razavi et al. | |
| 2012/0283794 A1 | 11/2012 | Kaib et al. | |
| 2012/0293323 A1 | 11/2012 | Kaib et al. | |
| 2012/0302860 A1 | 11/2012 | Volpe et al. | |
| 2012/0310315 A1 | 12/2012 | Savage et al. | |
| 2013/0085538 A1 | 4/2013 | Volpe et al. | |
| 2013/0231711 A1 | 9/2013 | Kaib | |
| 2013/0245388 A1 | 9/2013 | Rafferty et al. | |
| 2013/0274565 A1 | 10/2013 | Langer et al. | |
| 2013/0307685 A1 | 11/2013 | Sholder | |
| 2013/0317852 A1 | 11/2013 | Worrell et al. | |
| 2013/0325078 A1 | 12/2013 | Whiting et al. | |
| 2014/0025131 A1 | 1/2014 | Sullivan et al. | |
| 2014/0043149 A1 | 2/2014 | Cowan et al. | |
| 2014/0070957 A1 | 3/2014 | Longinotti-Buitoni et al. | |
| 2014/0142445 A1 | 5/2014 | Banet et al. | |
| 2014/0163663 A1 | 6/2014 | Poddar et al. | |
| 2014/0324112 A1 | 10/2014 | Macho et al. | |
| 2014/0378812 A1 | 12/2014 | Saroka et al. | |
| 2015/0039053 A1 | 2/2015 | Kaib et al. | |

(56) References Cited

U.S. PATENT DOCUMENTS

| | | | |
|---|---|---|---|
| 2015/0119725 A1 | 4/2015 | Martin et al. | |
| 2015/0238151 A1* | 8/2015 | Sitzman | A61B 5/363 600/483 |
| 2015/0328472 A1 | 11/2015 | Sullivan et al. | |
| 2016/0004831 A1 | 1/2016 | Carlson et al. | |
| 2016/0066801 A1 | 3/2016 | Kahlert et al. | |
| 2016/0067514 A1* | 3/2016 | Sullivan | A61B 5/0205 607/6 |
| 2016/0082277 A1 | 3/2016 | Foshee, Jr. et al. | |
| 2016/0135706 A1* | 5/2016 | Sullivan | A61B 5/316 600/509 |
| 2016/0287470 A1 | 10/2016 | Lewis et al. | |
| 2017/0014079 A1 | 1/2017 | Lee et al. | |
| 2017/0056682 A1 | 3/2017 | Kumar et al. | |
| 2017/0347899 A1* | 12/2017 | Bhushan | A61B 8/42 |
| 2018/0049649 A1 | 2/2018 | Addison et al. | |
| 2018/0199834 A1 | 7/2018 | Siedenburg | |
| 2018/0333058 A1 | 11/2018 | Coulon et al. | |
| 2019/0014997 A9 | 1/2019 | Siedenburg | |
| 2019/0030351 A1 | 1/2019 | Sullivan et al. | |
| 2019/0030352 A1 | 1/2019 | Sullivan et al. | |
| 2019/0168011 A1 | 6/2019 | Medema | |

OTHER PUBLICATIONS

American Heart Association "Blood Pressure vs. Heart Rate" last reviewed on Oct. 31, 2016, 2 pages.
Cheriyedath, Susha, "Photoplethsmography (PPG)" Feb. 27, 2019, 5 pages 5.
Coricidin HBP, "Understanding Blood Pressure Readings," Mar. 9, 2018, 5 pages.
Felizardo et al. "Blood Pressure Sensor Using NIRS" ECE4760: Final Project, Jan. 1, 2015, 8 pages.
Heartstart MRx and XL AED Algorithm—Application Note, Jul. 2001, Edition 2 Philips Healthcare, USA.
Kiernan, Clare, "Breakthrough opens door to $100 ultrasound machine," University of British Colombia, Sep. 11, 2018, 2 pages.
Kirstein et al., "A CMOS-based Tactile Sensor for Continuous Blood Pressure Monitoring" Proceeding of the Design, Automation and Test in Europe Conference and Exhibition, IEEE Computer Society, Oct. 24, 2007.
Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.
Laura Lovett, "Samsung's Galaxy S9 to Include Blood Pressure Monitor Research App", MOBILEHEALTHNEWS, Feb. 26, 2018.
LIFECOR LifeVest System Model WCD 3100 Operator's Manual, 2006, PN 20B0040 Rev FI, Zoll Lifecor Corporation, Pittsburgh, PA.
LifeVest Model 4000 Patient Manual, Zoll, 2009, PN 20B0047 Rev B.
Non-final office action dated Nov. 16, 2020, to U.S. Appl. No. 16/394,618.
OBS Medical, "Visensia, The Sixth Sense for Prediction," Document Reference: 011-0402-LMAN-F03, Jun. 2013.
Omron Blood Pressure Monitors for Upper Arm and Wrist, Mar. 9, 2018, 28 pages.
Pagan-Carlo, et al., "Encircling Overlapping Multipulse Shock Waveforms for Transthoracic Defibrillation," JACC Journals, Dec. 1998, vol. 32 Issue 7, p. 2065-2071.
ROHM "Optical Sensor for Heart Rate Monitor" BH1792GLC Product Detail, Jan. 1, 2015. 4 pages.
ROHM "Optical Sensor for Heart Rate Sensor IC" BH1790GLC Datasheet, Jan. 1, 2015, 25 pages.
Rohm Semiconductor, "ROHM and Equate Health Partner to Develop a Breakthrough Cuffless Optical Blood Pressure Monitor," Globe Newswire, Jan. 8, 2018.
ROHM Semiconductor, "ROHM's New High-Speed Optical Heart Rate Sensor Optimized for Measuring Blood Pressure, Stress and Vascular Age" Globe Newswire, Feb. 21, 2018.
Song et al., "Scan-E: An Optical Blood Pressure Sensor," ECE4760: Final Project, Cornell University Electrical & Computer Engineering, 2013.
The LifeVest Network/Patient Data Management System, Zoll, 2015, 2000503 Rev A.
Valencell, "The most advanced PPG sensors for wearables & hearables" Mar. 9, 2018, 10 pages.
Wang et al., "Cuff-Free Blood Pressure Estimation Using Pulse Transit Time and Heart Rate," Int Conf Signal Process Proc., Oct. 2014.
Zienkiewicz, Aleksandra, "Blood Pressure Estimation Using Pulse Transit Time Models", Master's Thesis Degree Programme in Computer Science and Engineering, Nov. 2017.

\* cited by examiner

SAMPLE COMPONENTS OF WEARABLE CARDIOVERTER DEFIBRILLATOR (WCD) SYSTEM

SAMPLE COMPONENTS OF EXTERNAL DEFIBRILLATOR

COMPONENTS OF
SAMPLE WCD SYSTEM

WEARABLE CARDIOVERTER DEFIBRILLATOR WITH A NON-INVASIVE BLOOD PRESSURE MONITOR

CROSS-REFERENCE TO RELATED APPLICATIONS

The present application is a continuation of U.S. application Ser. No. 16/394,618 filed Apr. 25, 2019, which in turn claims the benefit of U.S. Provisional Application No. 62/662,717 filed Apr. 25, 2018. Said application Ser. No. 16/394,618 and said Application No. 62/662,717 are hereby incorporated herein by reference in its entirety their entireties.

BACKGROUND

When people suffer from some types of heart arrhythmias, the result may be that blood flow to various parts of the body is reduced. Some arrhythmias may even result in a Sudden Cardiac Arrest (SCA). SCA can lead to death very quickly, for example within 10 minutes, unless treated in the interim.

Some people have an increased risk of SCA. Such people include patients who have had a heart attack, or a prior SCA episode. A frequent recommendation for these people is to receive an Implantable Cardioverter Defibrillator (ICD). The ICD is surgically implanted in the chest, and continuously monitors the patient's electrocardiogram (ECG). If certain types of heart arrhythmias are detected, then the ICD delivers an electric shock through the heart.

As a further precaution, people who have been identified to have an increased risk of an SCA are sometimes given a Wearable Cardioverter Defibrillator (WCD) system, to wear until the time that their ICD is implanted. Early versions of such systems were called wearable cardiac defibrillator systems. A WCD system typically includes a harness, vest, belt, or other garment that the patient is to wear. The WCD system further includes electronic components, such as a defibrillator and electrodes, coupled to the harness, vest, or other garment. When the patient wears the WCD system, the electrodes may make good electrical contact with the patient's skin, and therefore can help sense the patient's ECG. If a shockable heart arrhythmia is detected from the ECG, then the defibrillator delivers an appropriate electric shock through the patient's body, and thus through the heart. This may restart the patient's heart and thus save their life.

WCD systems analyze the patient's ECG data as part of the determination whether or not to apply a therapeutic electric shock to the patient. Since the patient can experience a change in blood flow during a heart arrhythmia episode, it can be beneficial to determine the patient's blood pressure and other patient parameters, for example to facilitate the shock determination algorithm.

DESCRIPTION OF THE DRAWING FIGURES

Claimed subject matter is particularly pointed out and distinctly claimed in the concluding portion of the specification. However, such subject matter may be understood by reference to the following detailed description when read with the accompanying drawings in which:

Figure 1:
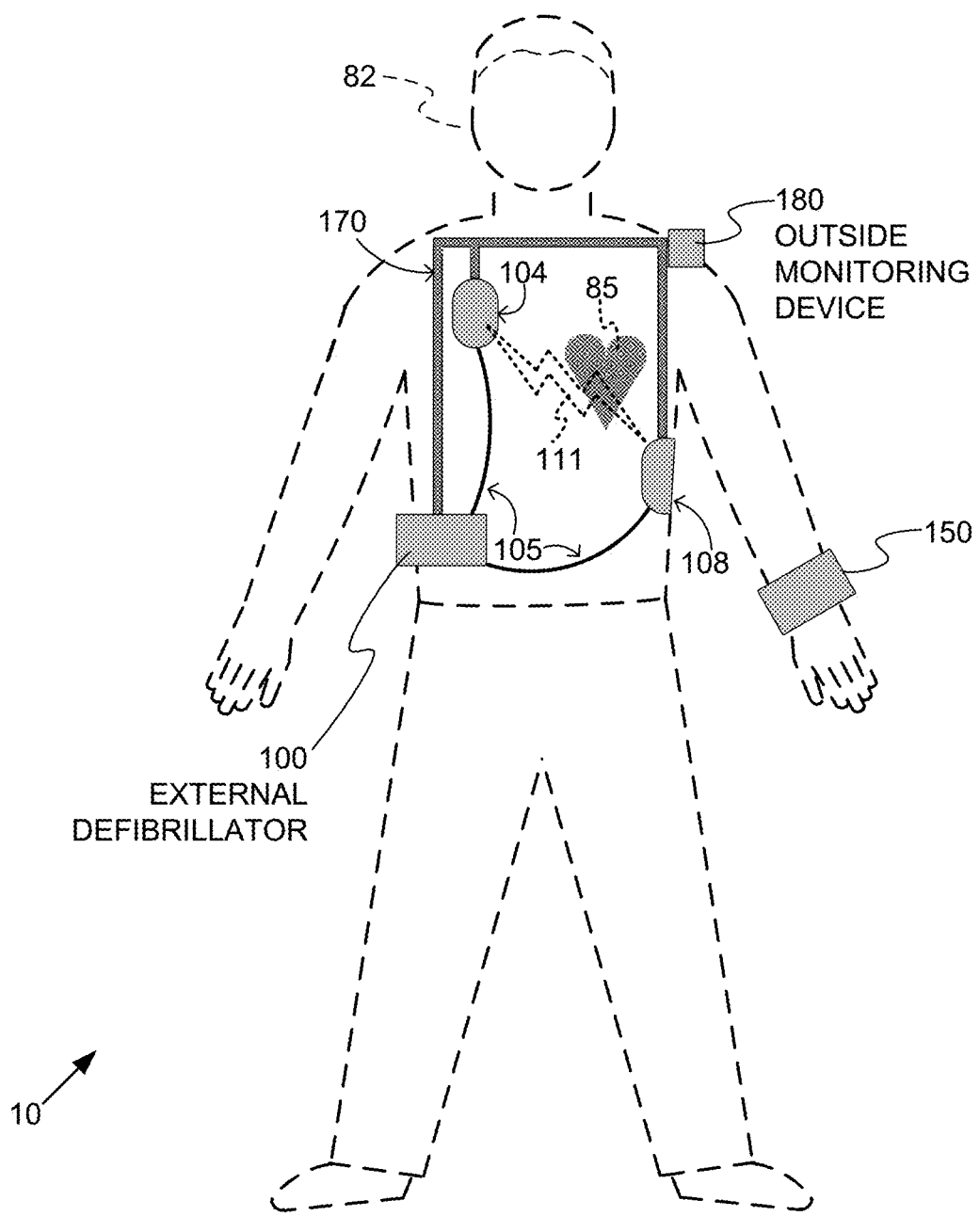
FIG. 1 is a diagram of components of a sample wearable cardioverter defibrillator (WCD) system incorporating a non-invasive blood pressure (NIBP) monitor in accordance with one or more embodiments.

It will be appreciated that for simplicity and/or clarity of illustration, elements illustrated in the figures have not necessarily been drawn to scale. For example, the dimensions of some of the elements may be exaggerated relative to other elements for clarity. Further, if considered appropriate, reference numerals have been repeated among the figures to indicate corresponding and/or analogous elements.

DETAILED DESCRIPTION

In the following detailed description, numerous specific details are set forth to provide a thorough understanding of claimed subject matter. It will, however, be understood by those skilled in the art that claimed subject matter may be practiced without these specific details. In other instances, well-known methods, procedures, components and/or circuits have not been described in detail.

In the following description and/or claims, the terms coupled and/or connected, along with their derivatives, may be used. In particular embodiments, connected may be used to indicate that two or more elements are in direct physical and/or electrical contact with each other. Coupled may mean that two or more elements are in direct physical and/or electrical contact. However, coupled may also mean that two or more elements may not be in direct contact with each other, but yet may still cooperate and/or interact with each other. For example, "coupled" may mean that two or more elements do not contact each other but are indirectly joined together via another element or intermediate elements. Finally, the terms "on," "overlying," and "over" may be used in the following description and claims. "On," "overlying," and "over" may be used to indicate that two or more elements are in direct physical contact with each other. It should be noted, however, that "over" may also mean that two or more elements are not in direct contact with each other. For example, "over" may mean that one element is above another element but not contact each other and may have another element or elements in between the two elements. Furthermore, the term "and/or" may mean "and", it may mean "or", it may mean "exclusive-or", it may mean "one", it may mean "some, but not all", it may mean "neither", and/or it may mean "both", although the scope of claimed subject matter is not limited in this respect. In the following description and/or claims, the terms "comprise" and "include," along with their derivatives, may be used and are intended as synonyms for each other.

FIG. 1 is a diagram of components of a sample wearable cardioverter defibrillator (WCD) system incorporating a non-invasive blood pressure (NIBP) monitor in accordance with one or more embodiments. A wearable cardioverter defibrillator (WCD) system 10 according to embodiments may protect an ambulatory patient by electrically restarting his or her heart if needed. Such a WCD system 10 may have a number of components. These components can be provided separately as modules that can be interconnected, or can be combined with other components, and so on.

FIG. 1 depicts a patient 82. Patient 82 may also be referred to as a person and/or wearer, since the patient is wearing components of the WCD system 10. Patient 82 is ambulatory, which means that, while wearing the wearable portion of the WCD system 10, patient 82 can walk around and is not necessarily bed-ridden. While patient 82 may be considered to be also a "user" of the WCD system 10, this is not a requirement. For instance, a user of the wearable cardioverter defibrillator (WCD) may also be a clinician such as a doctor, nurse, emergency medical technician (EMT) or other similarly tasked individual or group of individuals. In some cases, a user may even be a bystander. The particular context of these and other related terms within this description should be interpreted accordingly.

A WCD system 10 according to embodiments can be configured to defibrillate the patient 82 who is wearing the designated parts the WCD system 10. Defibrillating can be by the WCD system 10 delivering an electrical charge to the patient's body in the form of an electric shock. The electric shock can be delivered in one or more pulses.

FIG. 1 also depicts components of a WCD system 10 made according to embodiments. One such component is a support structure 170, or garment, that is wearable by ambulatory patient 82. Accordingly, support structure 170 is configured to be worn by ambulatory patient 82 for at least several hours per day, and for at least several days, even a few months. It will be understood that support structure 170 is shown only generically in FIG. 1, and in fact partly conceptually. FIG. 1 is provided merely to illustrate concepts about support structure 170, and is not to be construed as limiting how support structure 170 is implemented, or how it is worn.

Support structure 170 can be implemented in many different ways. For example, it can be implemented in a single component or a combination of multiple components. In embodiments, support structure 170 could include a vest, a half-vest, a garment, etc. In such embodiments such items can be worn similarly to analogous articles of clothing. In embodiments, support structure 170 could include a harness, one or more belts or straps, etc. In such embodiments, such items can be worn by the patient around the torso, hips, over the shoulder, etc. In embodiments, support structure 170 can include a container or housing, which can even be waterproof. In such embodiments, the support structure can be worn by being attached to the patient's body by adhesive material, for example as shown and described in U.S. Pat. No. 8,024,037 which is incorporated herein by reference in its entirety. Support structure 170 can even be implemented as described for the support structure of U.S. application Ser. No. 15/120,655, published as US 2017/0056682 A1, which is incorporated herein by reference in its entirety. In such embodiments, the person skilled in the art will recognize that additional components of the WCD system 10 can be in the housing of a support structure instead of being attached externally to the support structure, for example as described in the US 2017/0056682 A1 document. There can be other examples.

FIG. 1 shows a sample external defibrillator 100. As described in more detail later in this document, some aspects of external defibrillator 100 include a housing and an energy storage module within the housing. As such, in the context of a WCD system 10, defibrillator 100 is sometimes called a main electronics module or a monitor. The energy storage module can be configured to store an electrical charge. Other components can cause at least some of the stored electrical charge to be discharged via electrodes through the patient to deliver one or more defibrillation shocks through the patient 82.

FIG. 1 also shows sample defibrillation electrodes 104 and/or 108, which are coupled to external defibrillator 100 via electrode leads 105. Defibrillation electrodes 104 and/or 108 can be configured to be worn by patient 82 in several ways. For instance, defibrillator 100 and defibrillation electrodes 104 and/or 108 can be coupled to support structure 170, directly or indirectly. In other words, support structure 170 can be configured to be worn by ambulatory patient 82 to maintain at least one of electrodes 104 and/or 108 on the body of ambulatory patient 82, while patient 82 is moving around, etc. The electrode can be thus maintained on the body by being attached to the skin of patient 82, simply pressed against the skin directly or through garments, etc. In some embodiments the electrode is not necessarily pressed against the skin, but becomes biased that way upon sensing a condition that could merit intervention by the WCD system 10. In addition, many of the components of defibrillator 100 can be considered coupled to support structure 170 directly, or indirectly via at least one of defibrillation electrodes 104 and/or 108.

When defibrillation electrodes 104 and/or 108 make good electrical contact with the body of patient 82, defibrillator 100 can administer, via electrodes 104 and/or 108, a brief, strong electric pulse 111 through the body. Pulse 111 is also known as shock, defibrillation shock, therapy, electrotherapy, therapy shock, etc. Pulse 111 is intended to go through and restart heart 85, in an effort to save the life of patient 82. Pulse 111 can further include one or more pacing pulses of lesser magnitude to simply pace heart 85 if needed, and so on.

A typical defibrillator decides whether to defibrillate or not based on an ECG signal of the patient. External defibrillator 100, however, may initiate defibrillation, or hold-off defibrillation, based on a variety of inputs, with the ECG signal merely being one of these inputs.

A WCD system 10 according to embodiments can obtain data from patient 82. For collecting such data, the WCD system 10 may optionally include at least an outside monitoring device 180. Device 180 is called an "outside" device because it could be provided as a standalone device, for example not within the housing of defibrillator 100. Device 180 can be configured to sense or monitor at least one local parameter. A local parameter can be a parameter of patient 82, or a parameter of the WCD system 10, or a parameter of the environment, as will be described later in this document. In some embodiments, outside monitoring device 180 can comprise a hub or similar device through which connections and/or leads may be made of the various components of the WCD system 100. For example, at least some of the leads of external defibrillator 100 may be connected to and/or routed through the outside monitoring device 180 including, for example, one or more ECG leads, a right-leg drive (RLD) lead, leads connected to the defibrillation electrodes 104 and/or 108, and so on. In some embodiments, outside monitoring device 180 can include a controller or processor that is used to implement at least a portion of the shock/no-shock algorithm to determine whether a shock should or should not be applied to the patient 82, although the scope of the disclosed subject matter is not limited in this respect.

For some of these parameters, device 180 may include one or more sensors or transducers. Each one of such sensors can be configured to sense a parameter of patient 82, and to render an input responsive to the sensed parameter. In some embodiments the input is quantitative, such as values of a sensed parameter. In other embodiments the input is qualitative, such as informing whether or not a threshold is crossed, and so on. Sometimes these inputs about patient 82 are also called physiological inputs and patient inputs. In embodiments, a sensor can be construed more broadly, as encompassing many individual sensors.

Optionally, device 180 is physically coupled to support structure 170. In addition, device 180 may be communicatively coupled with other components that are coupled to support structure 170. Such communication can be implemented by a communication module, as will be deemed applicable by a person skilled in the art in view of this description.

In embodiments, one or more of the components of the shown WCD system 10 may be customized for patient 82. This customization may include a number of aspects. For instance, support structure 170 can be fitted to the body of patient 82. For another instance, baseline physiological parameters of patient 82 can be measured, such as the heart rate of patient 82 while resting, while walking, motion detector outputs while walking, etc. The measured values of such baseline physiological parameters can be used to customize the WCD system 10, in order to make its diagnoses more accurate, since patients' bodies differ from one another. Of course, such parameter values can be stored in a memory of the WCD system 10, and so on. Moreover, a programming interface can be made according to embodiments, which receives such measured values of baseline physiological parameters. Such a programming interface may input automatically in the WCD system 10 these, along with other data.

In one or more embodiments, WCD system 10 may include a non-invasive blood pressure (NIBP) monitor 150 that is capable of monitoring the blood pressure of the patient 82 as one or more of the patient parameters collected by WCD system 10. The NIBP monitor 150 can be referred to as non-invasive since the monitor is capable of obtaining a blood pressure reading of the patient 82 without insertion of catheter into a patient's blood vessel. In some embodiments, NIBP monitor 150 can be referred to as a cuff-less NIBP monitor 150 in that it is capable of obtaining a blood pressure reading without using a conventional cuff device placed around the patient's arm that is inflated and deflated to obtain the measurement. Furthermore, the NIBP 150 monitor is capable of obtaining frequent blood pressure measurements while the patient 82 is wearing the monitor through the day and/or during the night when the patient 82 is sleeping.

The NIBP monitor 150 may be provided in various types of form factors to be placed on the patient's body at various locations and/or to integrate with WCD system 10 in various ways. For example, in some embodiments, NIBP monitor 150 may be worn on the wrist of the patient 82 or various other locations on the patient 82 such as on the arm, leg, ankle, chest, or back of the patient 82 depending on the provided form factor and/or technology utilized by the NIBP monitor 150 to obtain a blood pressure reading.

In some embodiments, NIBP monitor 150 may be incorporated into an external device or accessory such as a smartphone. Such devices may employ an optical NIBP sensor. Such devices may come in various other form factors such as a patch, watch, earring, eye glasses, ankle bracelet, and so on, wherein the NIBP monitor 150 can be unobtrusive and in location in which the patient's vasculature may be near the skin so that the optical sensor of this type of NIBP monitor 150 can obtain good readings.

In some embodiments, the NIBP monitor 150 can include an optical based NIBP sensor built into the alert button or stop button of the WCD system 10 wherein the alert button or stop button is used by the patient 82 to stop an impending shock if the patient so desires. In such embodiments, the patient is already aware of the location of the alert button or stop button which would provide a simple and readily available device for the patient to use to take a blood pressure measurement. In addition, when the NIBP monitor 150 is in the alert button or stop button, the patient's blood pressure can be obtained whenever the patient 82 needs to abort a shock.

In one or more embodiments, the NIBP monitor 150 can include or otherwise comprise an optical pulse oximetry sensor and/or a methemoglobin sensor wherein optical NIBP sensor functionality can be implemented using a pulse oximetry or methemoglobin sensor. In other embodiments, a cuff-less NIBP monitor 150 can be incorporated in one or more of the ECG electrodes of the WCD system 10. Such an NIBP sensor can be an optical sensor as described above, or an electro-mechanical sensor such as described in "A CMOS-based Tactile Sensor for Continuous Blood Pressure Monitoring", Kirstein, Sedivy, et al., Proceedings of the Design, Automation and Test in Europe Conference and Exhibition, 1530-1591/05 (March 2005) which is incorporated herein by reference in its entirety.

In other embodiments, the NIBP monitor 150 can be adapted for use in proposed adhesive type defibrillators as disclosed in U. S. Pat. No. 8,024,037. For example, the NIBP monitor 150 can be disposed in one of the adhesive modules as shown in the '037 patent, or in an "appendage" or "flap" that extends from the module so that the NIBP monitor 150 is positioned on an appropriate location on the patient. Embodiments of a cuff-less NIBP sensor can include a wireless communication interface such as BLUETOOTH, near-field communication (NFC), Wi-Fi DIRECT, ZIGBEE, and so on, to transmit the blood pressure data to a module of the WCD system 10, to a personal communication device of the WCD system 10 for example as disclosed in U.S. Pat. No. 8,838,235, or to another remote device. Said U.S. Pat. No. 8,838,235 is incorporated herein by reference in its entirety. In some embodiments, a wired communication link can be used instead of a wireless communication link. For example, the NIBP monitor 150 can be implemented in an electrode that can be configured so that the blood pressure data is transmitted on a wire bundled with the wire or wires of the electrode sensors, or multiplexed on the same wire as the electrode data, and so on.

Figure 2:
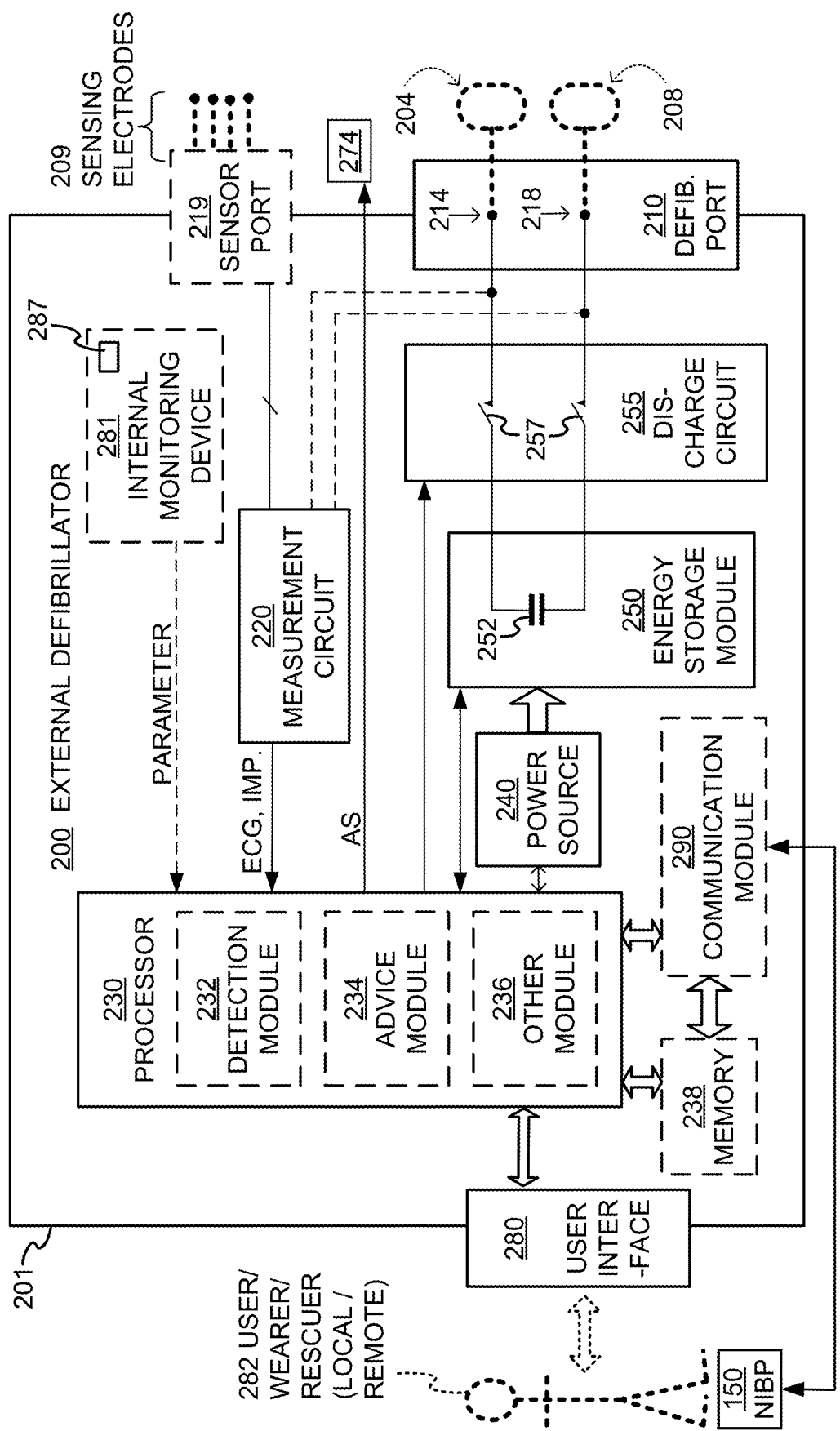
FIG. 2 is a diagram showing sample components of an external defibrillator, such as the one belonging in the system of FIG. 1, including an NIBP monitor in accordance with one or more embodiments.

FIG. 2 is a diagram showing sample components of an external defibrillator, such as the one belonging in the system of FIG. 1, including an NIBP monitor in accordance with one or more embodiments. Some components of WCD system 10 can be, for example, included in external defibrillator 100 of FIG. 1. The components shown in FIG. 2 can be provided in a housing 201, which may also be referred to as casing 201.

External defibrillator 200 is intended for a patient who would be wearing it, such as ambulatory patient 82 of FIG. 1. Defibrillator 200 may further include a user interface 280 for a user 282. User 282 can be patient 82, also known as wearer 82. Alternatively, user 282 can be a local rescuer at the scene, such as a bystander who might offer assistance, or a trained person. Alternatively, user 282 might be a remotely located trained caregiver in communication with the WCD system 10.

User interface 280 can be made in a number of ways. User interface 280 may include output devices, which can be visual, audible or tactile, for communicating to a user 282 by outputting images, sounds or vibrations. Images, sounds, vibrations, and anything that can be perceived by user 282 can also be called human-perceptible indications (HPIs). There are many examples of output devices. For example, an output device can be a light, or a screen to display what is sensed, detected and/or measured, and provide visual feedback to user 282 acting as a rescuer for their resuscitation attempts, and so on. Another output device can be a speaker, which can be configured to issue voice prompts, beeps, loud alarm sounds and/or words to warn bystanders, etc.

User interface 280 further may include input devices for receiving inputs from users. Such input devices may include various controls, such as pushbuttons, keyboards, touchscreens, one or more microphones, and so on. An input device can be a cancel switch, which is sometimes called an "I am alive" switch or "live man" switch. In some embodiments, actuating the cancel switch can prevent the impending delivery of a shock and may be referred to as a stop button in such embodiments.

Defibrillator 200 may include an internal monitoring device 281. Device 281 is called an "internal" device because it is incorporated within housing 201. Monitoring device 281 can sense or monitor patient parameters such as patient physiological parameters, system parameters and/or environmental parameters, all of which can be called patient data. In other words, internal monitoring device 281 can be complementary or an alternative to outside monitoring device 180 of FIG. 1. Allocating which of the parameters are to be monitored by which of monitoring devices 180, 281 can be done according to design considerations. Device 281 may include one or more sensors as also described elsewhere in this document.

Patient parameters may include patient physiological parameters. Patient physiological parameters may include, for example and without limitation, those physiological parameters that can be of any help in detecting by the WCD system 10 whether or not the patient is in need of a shock or other intervention or assistance. Patient physiological parameters may also optionally include the patient's medical history, event history, and so on. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, monitoring device 180 and/or monitoring device 281 may include one or more sensors configured to acquire patient physiological signals. Examples of such sensors or transducers include one or more electrodes to detect ECG data, a perfusion sensor, a pulse oximeter, a device for detecting blood flow (e.g. a Doppler device), a sensor for detecting blood pressure (e.g. a cuff), an optical sensor, illumination detectors and sensors perhaps working together with light sources for detecting color change in tissue, a motion sensor, a device that can detect heart wall movement, a sound sensor, a device with a microphone, an SpO2 sensor, and so on. In accordance with one or more embodiments, monitoring device 180 and/or monitoring device 281 may include a cuff-less non-invasive blood pressure (NIBP) monitor and may tangibly embody one or more embodiments of NIBP monitor 150 or may operate in conjunction with NIBP monitor 150, and the scope of the disclosed subject matter is not limited in this respect. In view of this disclosure, it will be appreciated that such sensors can help detect the patient's pulse, and can therefore also be called pulse detection sensors, pulse sensors, and pulse rate sensors. In addition, a person skilled in the art may implement other ways of performing pulse detection.

In some embodiments, the local parameter is a trend that can be detected in a monitored physiological parameter of patient 282. A trend can be detected by comparing values of parameters at different times over short and long terms. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from SpO2, CO2, or other parameters such as those mentioned above; f) respiratory function, respiratory rate, etc.; g) motion, level of activity; and so on. Once a trend is detected, it can be stored and/or reported via a communication link, optionally along with a warning if warranted. From the report, a physician monitoring the progress of patient (user) 282 will know about a condition that is either not improving or deteriorating.

Patient state parameters include recorded aspects of patient (user) 282, such as motion, posture, whether they have spoken recently plus maybe also what they said, and so on, plus optionally the history of these parameters. Alternatively, one of these monitoring devices could include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether sudden cardiac arrest (SCA) is indeed taking place.

A WCD system 10 made according to embodiments may thus include a motion detector 287. In embodiments, a motion detector can be implemented within monitoring device 180 or monitoring device 281. Such a motion detector can be made in many ways as is known in the art, for example by using an accelerometer. In this example, a motion detector 287 is implemented within monitoring device 281. A motion detector of a WCD system 10 according to embodiments can be configured to detect a motion event. A motion event can be defined as is convenient, for example a change in motion from a baseline motion or rest, etc. In such cases, a sensed patient parameter can include motion.

System parameters of a WCD system 10 can include system identification, battery status, system date and time, reports of self-testing, records of data entered, records of episodes and intervention, and so on. In response to the detected motion event, the motion detector may render or generate, from the detected motion event or motion, a motion detection input that can be received by a subsequent device or functionality.

Environmental parameters can include ambient temperature and pressure. Moreover, a humidity sensor may provide information as to whether or not it is likely raining. Presumed patient location could also be considered an environmental parameter. The patient location could be presumed or determined, if monitoring device 180 and/or monitoring device 281 includes a GPS location sensor as described above, and if it is presumed that the patient is wearing the WCD system 10.

Defibrillator 200 typically includes a defibrillation port 210, which can be a socket in housing 201. Defibrillation port 210 includes electrical node 214 and/or electrical node 218. Leads of defibrillation electrode 204 and/or defibrillation electrode 208, such as leads 105 of FIG. 1, can be plugged into defibrillation port 210 so as to make electrical contact with node 214 and node 218, respectively. It is also possible that defibrillation electrode 204 and/or defibrillation electrode 208 instead are connected continuously to defibrillation port 210. Either way, defibrillation port 210 can be used for guiding, via electrodes, to the wearer at least some of the electrical charge that has been stored in an energy storage module 250 that is described more fully later in this document. The electric charge will be the shock for defibrillation, pacing, and so on.

Defibrillator 200 may optionally also have a sensor port 219 in housing 201, which is also sometimes known as an ECG port. Sensor port 219 can be adapted for plugging in sensing electrodes 209, which are also known as ECG electrodes and ECG leads. It is also possible that sensing electrodes 209 can be connected continuously to sensor port 219, instead. Sensing electrodes 209 are types of transducers that can help sense an ECG signal, e.g. a 12-lead signal, or a signal from a different number of leads, especially if the leads make good electrical contact with the body of the patient and in particular with the skin of the patient. As with defibrillation electrodes 204 and/or 208, the support structure 170 can be configured to be worn by patient 282 so as to maintain sensing electrodes 209 on a body of patient (user) 282. For example, sensing electrodes 209 can be attached to the inside of support structure 170 for making good electrical contact with the patient, similarly with defibrillation electrodes 204 and/or 208.

Optionally a WCD system 10 according to embodiments also includes a fluid that can be deployed automatically between the electrodes and the patient's skin. The fluid can be conductive, such as by including an electrolyte, for establishing a better electrical contact between the electrodes and the skin. Electrically speaking, when the fluid is deployed, the electrical impedance between each electrode and the skin is reduced. Mechanically speaking, the fluid may be in the form of a low-viscosity gel so that it does not flow away after being deployed from the location it is released near the electrode. The fluid can be used for both defibrillation electrodes 204 and/or 208, and for sensing electrodes 209.

The fluid may be initially stored in a fluid reservoir, not shown in FIG. 2. Such a fluid reservoir can be coupled to the support structure 170. In addition, a WCD system 10 according to embodiments further includes a fluid deploying mechanism 274. Fluid deploying mechanism 274 can be configured to cause at least some of the fluid to be released from the reservoir, and be deployed near one or both of the patient locations to which electrodes 204 and/or 208 are configured to be attached to the patient. In some embodiments, fluid deploying mechanism 274 is activated prior to the electrical discharge responsive to receiving activation signal (AS) from a processor 230, which is described more fully later in this document.

In some embodiments, defibrillator 200 also includes a measurement circuit 220, as one or more of its working together with its sensors or transducers. Measurement circuit 220 senses one or more electrical physiological signals of the patient from sensor port 219, if provided. Even if defibrillator 200 lacks sensor port 219, measurement circuit 220 optionally may obtain physiological signals through nodes 214 and/or 218 instead, when defibrillation electrodes 204 and/or 208 are attached to the patient. In these embodiments, the input reflects an ECG measurement. The patient parameter can be an ECG, which can be sensed as a voltage difference between electrodes 204 and 208. In addition, the patient parameter can be an impedance, which can be sensed between electrodes 204 and 208 and/or between the connections of sensor port 219 considered pairwise. Sensing the impedance can be useful for detecting, among other things, whether these electrodes 204 and/or 208 and/or sensing electrodes 209 are not making good electrical contact with the patient's body. These patient physiological signals may be sensed when available. Measurement circuit 220 can then render or generate information about them as inputs, data, other signals, etc. As such, measurement circuit 220 can be configured to render a patient input responsive to a patient parameter sensed by a sensor. In some embodiments, measurement circuit 220 can be configured to render a patient input, such as values of an ECG signal, responsive to the ECG signal sensed by sensing electrodes 209. More strictly speaking, the information rendered by measurement circuit 220 is output from it, but this information can be called an input because it is received as an input by a subsequent device or functionality.

Defibrillator 200 also includes a processor 230. Processor 230 may be implemented in a number of ways. Such ways include, by way of example and not of limitation, digital and/or analog processors such as microprocessors and Digital Signal Processors (DSPs), controllers such as microcontrollers, software running in a machine, programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 230 may include, or have access to, a non-transitory storage medium, such as memory 238 that is described more fully later in this document. Such a memory 238 can have a non-volatile component for storage of machine-readable and machine-executable instructions. A set of such instructions can also be called a program. The instructions, which may also be referred to as "software," generally provide functionality by performing acts, operations and/or methods as may be disclosed herein or understood by one skilled in the art in view of the disclosed embodiments. In some embodiments, and as a matter of convention used herein, instances of the software may be referred to as a "module" and by other similar terms. Generally, a module includes a set of the instructions to offer or fulfill a particular functionality. Embodiments of modules and the functionality delivered are not limited by the embodiments described in this document.

Processor 230 can be considered to have a number of modules. One such module can be a detection module 232. Detection module 232 can include a Ventricular Fibrillation (VF) detector. The patient's sensed ECG from measurement circuit 220, which can be available as inputs, data that reflect values, or values of other signals, may be used by the VF detector to determine whether the patient is experiencing VF. Detecting VF is useful because VF typically results in sudden cardiac arrest (SCA). Detection module 232 can also include a Ventricular Tachycardia (VT) detector, and so on.

Another such module in processor 230 can be an advice module 234, which generates advice for what to do. The advice can be based on outputs of detection module 232.

There can be many types of advice according to embodiments. In some embodiments, the advice is a shock/no shock determination that processor 230 can make, for example via advice module 234. The shock/no shock determination can be made by executing a stored Shock Advisory Algorithm (SAA). A Shock Advisory Algorithm can make a shock/no shock determination from one or more ECG signals that are captured according to embodiments, and determine whether or not a shock criterion is met. The determination can be made from a rhythm analysis of the captured ECG signal or otherwise.

In some embodiments, when the determination is to shock, an electrical charge is delivered to the patient. Delivering the electrical charge is also known as discharging and shocking the patient. As mentioned above, such can be for defibrillation, pacing, and so on.

In good or ideal conditions, a very reliable shock/no shock determination can be made from a segment of the sensed ECG signal of the patient. In practice, however, the ECG signal is often corrupted by electrical noise, which can make it difficult to analyze. Too much noise sometimes causes an incorrect detection of a heart arrhythmia, resulting in a false alarm to the patient. Noisy ECG signals may be handled as described in U.S. application Ser. No. 16/037,990, filed on Jul. 17, 2018 and since published as US 2019/0030351 A1, and in U.S. application Ser. No. 16/038,007, filed on Jul. 17, 2018 and since published as US 2019/0030352 A1, both by the same applicant and incorporated herein by reference in their entireties.

Processor 230 can include additional modules, such as other module 236, for other functions. In addition, if internal monitoring device 281 is provided, processor 230 may receive its inputs, etc.

Defibrillator 200 optionally further includes a memory 238, which can work together with processor 230. Memory 238 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. Memory 238 is thus a non-transitory storage medium. Memory 238, if provided, can include programs and/or instructions for processor 230, which processor 230 may be able to read and execute. More particularly, the programs can include sets of instructions in the form of code, which processor 230 may be able to execute upon reading. Executing is performed by physical manipulations of physical quantities, and may result in functions, operations, processes, acts, actions and/or methods to be performed, and/or the processor to cause other devices or components or blocks to perform such functions, operations, processes, acts, actions and/or methods. The programs can be operational for the inherent needs of processor 230, and can also include protocols and ways that decisions can be made by advice module 234. In addition, memory 238 can store prompts for user 282, if this user is a local rescuer. Moreover, memory 238 can store data. This data can include patient data, system data and environmental data, for example as learned by internal monitoring device 281 and outside monitoring device 180. The data can be stored in memory 238 before it is transmitted out of defibrillator 200, or be stored there after it is received by defibrillator 200.

Defibrillator 200 can optionally include a communication module 290, for establishing one or more wired and/or wireless communication links with other devices of other entities, such as a remote assistance center, Emergency Medical Services (EMS), and so on. The communication module 290 may include short range wireless communication circuitry for example in accordance with a BLUETOOTH or ZIGBEE standard, short or medium range wireless communication for example a W-Fi or wireless local area network (WLAN) in accordance with an Institute of Electrical and Electronics Engineers (IEEE) 802.11x standard, or a wireless wide area network (WWAN) in accordance with a Third Generation Partnership Project (3GPP) including a 3G, 4G, or 5G New Radio (NR) standard. The communication links can be used to transfer data and commands. The data may be patient data, event information, therapy attempted, cardiopulmonary resuscitation (CPR) performance, system data, environmental data, and so on. For example, communication module 290 may transmit wirelessly, e.g. on a daily basis, heart rate, respiratory rate, and other vital signs data to a server accessible over the internet, for instance as described in U.S. application Ser. No. 13/959,894 filed Aug. 6, 2012 and published as US 2014/0043149 A1 and which is incorporated herein by reference in its entirety. This data can be analyzed directly by the patient's physician and can also be analyzed automatically by algorithms designed to detect a developing illness and then notify medical personnel via text, email, phone, etc. Module 290 may also include such interconnected sub-components as may be deemed necessary by a person skilled in the art, for example an antenna, portions of a processor, supporting electronics, outlet for a telephone or a network cable, etc. Furthermore, in accordance with one or more embodiments, NIBP 150 can couple with communication module 290 of defibrillator 200 via a wired or wireless communication link. In some embodiments, NIBP 150 can couple with defibrillator 200 via outside monitoring device 180 of FIG. 1 acting as an intermediate device, connector, bus, router, switch, or hub, and the scope of the disclosed subject matter is not limited in this respect.

Defibrillator 200 also may include a power source 240. To enable portability of defibrillator 200, power source 240 typically includes a battery. Such a battery typically can be implemented as a battery pack, which can be rechargeable or not. Sometimes a combination of rechargeable and non-rechargeable battery packs is provided. Other embodiments of power source 240 can include an alternating current (AC) power override, for where AC power will be available, an energy-storing capacitor or bank of capacitors, and so on. Appropriate components may be included to provide for charging or replacing power source 240. In some embodiments, power source 240 is controlled and/or monitored by processor 230.

Defibrillator 200 additionally may include an energy storage module 250. Energy storage module 250 can be coupled to the support structure 170 of the WCD system 10, for example either directly or via the electrodes and their leads. Module 250 is where some electrical energy can be stored temporarily in the form of an electrical charge when preparing it for discharge to administer a shock. In some embodiments, module 250 can be charged from power source 240 to the desired amount of energy as controlled by processor 230. In typical implementations, module 250 includes a capacitor 252 which can be a single capacitor or a system or bank of capacitors, and so on. In some embodiments, energy storage module 250 includes a device that exhibits high power density such as an ultracapacitor. As described above, capacitor 252 can store the energy in the form of an electrical charge for delivering to the patient.

A decision to shock can be made responsive to the shock criterion being met, as per the above-mentioned determination. When the decision is to shock, processor 230 can be configured to cause at least some or all of the electrical charge stored in module 250 to be discharged through patient 82 while the support structure is worn by patient 82 so as to deliver a shock 111 to patient 82.

For causing the discharge, defibrillator 200 can include a discharge circuit 255. When the decision is to shock, processor 230 can be configured to control discharge circuit 255 to discharge through the patient 82 at least some or all of the electrical charge stored in energy storage module 250. Discharging can be to nodes 214 and/or 218, and from there to defibrillation electrodes 204 and/or 208, so as to cause a shock to be delivered to the patient. Circuit 255 can include one or more switches 257. Switches 257 can be made in a number of ways, such as by an H-bridge, and so on. Circuit 255 could also be thus controlled via processor 230, and/or user interface 280.

A time waveform of the discharge may be controlled by thus controlling discharge circuit 255. The amount of energy of the discharge can be controlled by how much energy storage module has been charged, and by how long discharge circuit 255 is controlled to remain open. Defibrillator 200 optionally can include other components.

Figure 3:
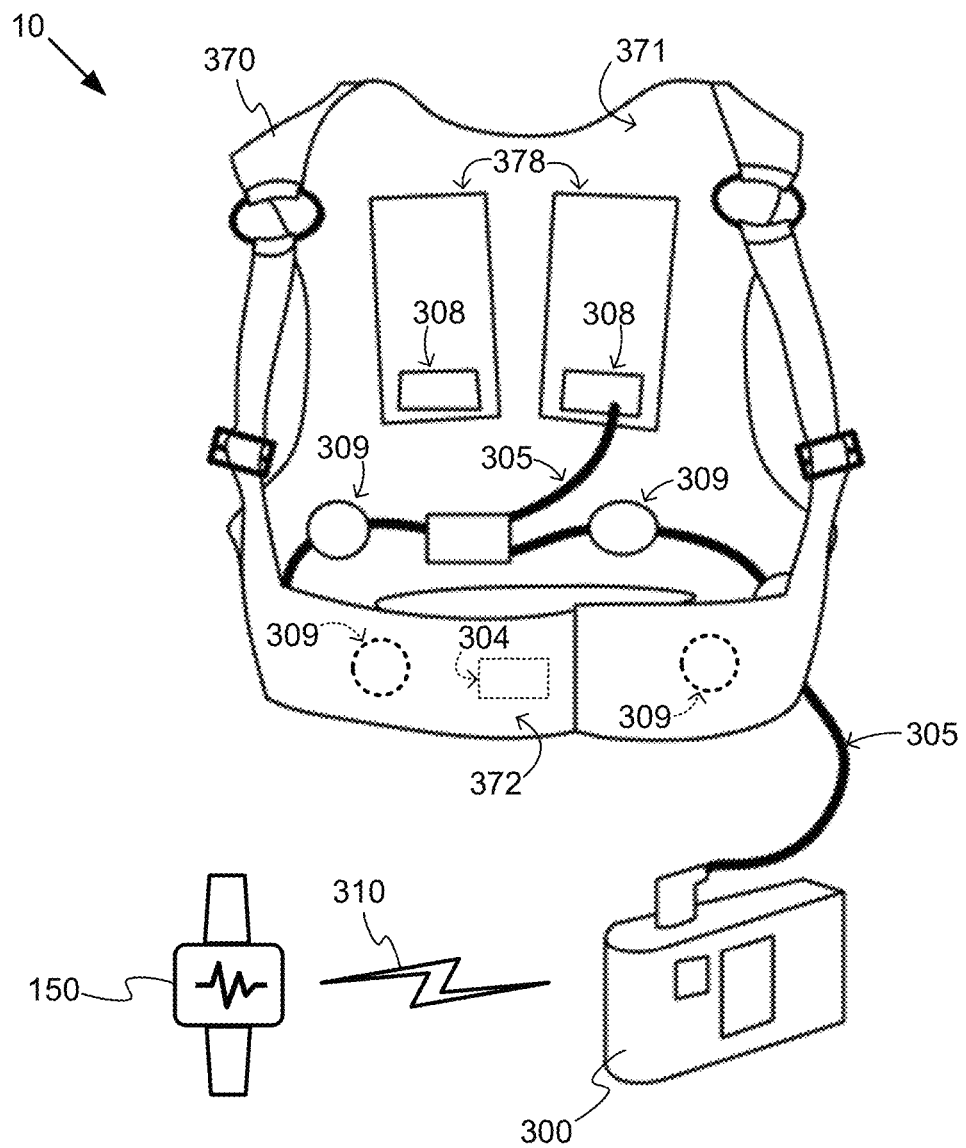
FIG. 3 is a diagram of sample embodiments of components of a WCD system and an NIBP monitor in accordance with one or more embodiments.

FIG. 3 is a diagram of sample embodiments of components of a WCD system 10 and an NIBP monitor in accordance with one or more embodiments. A support structure 370 includes a vest-like wearable garment. Support structure 370 has a back side 371, and a front side 372 that closes in front of the chest of the patient.

The WCD system 10 of FIG. 3 also includes an external defibrillator 300. FIG. 3 does not show any support for external defibrillator 300, which may be carried in a purse, on a belt, by a strap over the shoulder, and so on. Wires 305 connect external defibrillator 300 to electrodes 304, 308, and/or 309. Of those, electrodes 304 and 308 are defibrillation electrodes, and electrodes 309 are ECG sensing electrodes.

Support structure 370 is configured to be worn by the ambulatory patient to maintain electrodes 304, 308, and/or 309 on a body of the patient. Back defibrillation electrodes 308 can be maintained in pockets 378. The inside of pockets 378 can be made with loose netting, so that electrodes 308 can contact the back of the patient 82, especially with the help of the conductive fluid that has been deployed in such embodiments. In addition, sensing electrodes 309 are maintained in positions that surround the patient's torso, for sensing ECG signals and/or the impedance of the patient 82.

ECG signals in a WCD system 10 may include too much electrical noise to be useful. To ameliorate the problem, multiple ECG sensing electrodes 309 are provided, for presenting many options to processor 230. These options are different vectors for sensing the ECG signal, as described in more detail below.

In accordance with one or more embodiments, NIPB monitor 150 can communicate with external defibrillator 300, for example via a wireless communication link 310 in some embodiments. In other embodiments, NIBP monitor 150 also can communicate with external defibrillator 300 via a wired communication link, and the scope of the disclosed subject matter is not limited in this respect. Various example embodiments of how NIBP monitor 150 can communicate with WCD system 10 are shown in and described with respect to FIG. 4, below.

Figure 4:
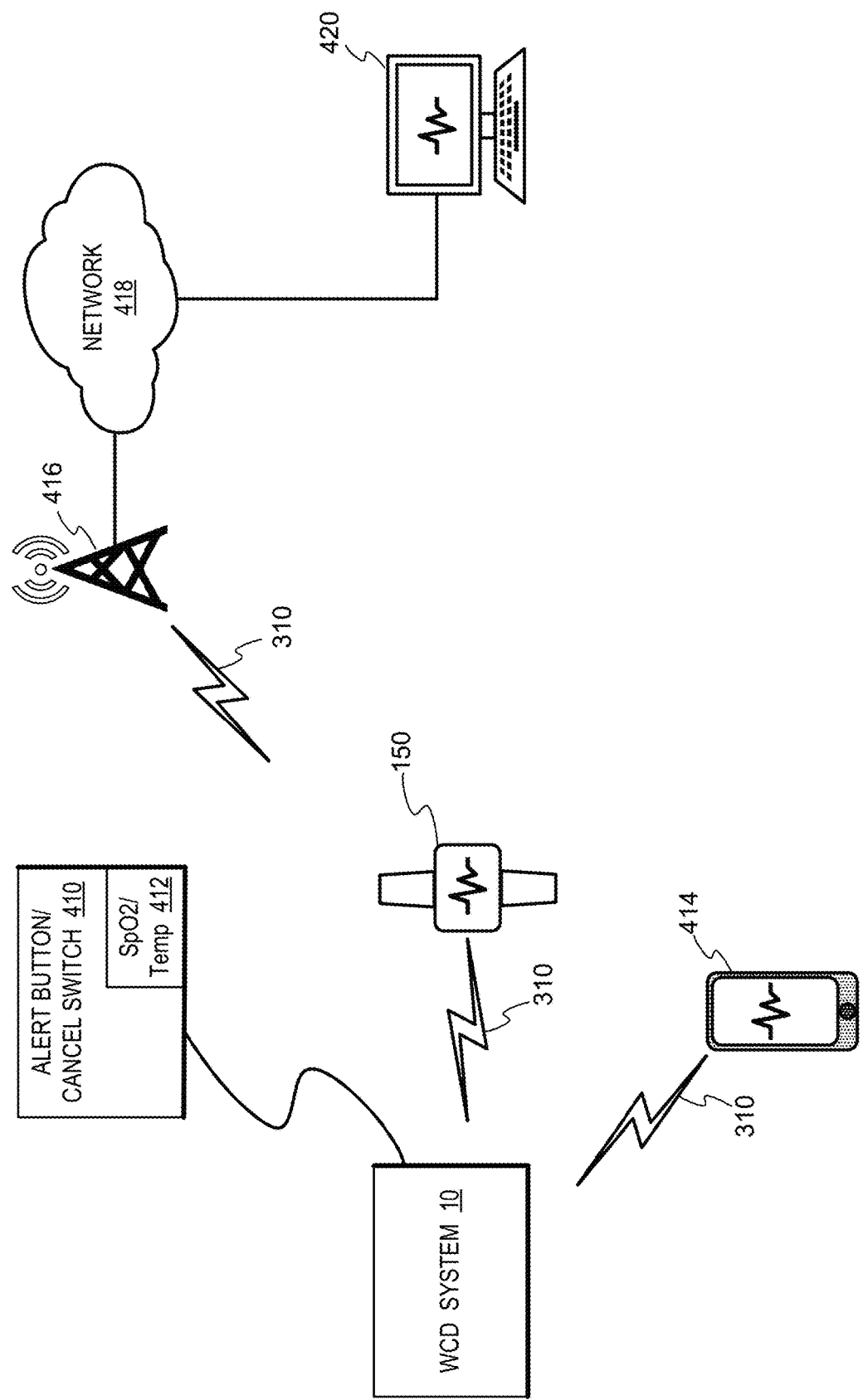
FIG. 4 is a diagram of example system in which blood pressure data and SpO2 data can be collected with a WCD and saved or transmitted to a remote device via a network in accordance with one or more embodiments.

FIG. 4 is a diagram of example system in which blood pressure data and SpO2 data can be collected with a WCD and saved or transmitted to a remote device via a network in accordance with one or more embodiments. As shown in FIG. 4, NIBP monitor 150 is capable of obtaining blood pressure data and/or peripheral capillary oxygen saturation (SpO2) data from a patient 82 and is able to transmit the collected patient data to WCD system 10 via wireless communication link 310. In some embodiments, NIBP monitor 150 can be worn somewhere on the patient's body such as on a wrist, and ankle, and so on. In some embodiments, an SpO2 sensor and/or temperature sensor 412 may be located in the alert button, or cancel or stop switch, 410 that is coupled with the WCD system 10. Since SpO2 sensors typically are configured to take a reading from a patient's fingertip, this type of sensor can easily be incorporated into the alert button 412 mechanism or housing. Additionally, in some embodiments, one or more sensors can be integrated into an external device such as a smartphone 414 that is capable of collecting patient data and transmitting the patient data to WCD system 10. The WCD system 10 may include storage such as memory 238 of FIG. 2 in which collected patient data can be stored for later retrieval and analysis by medical personnel working with the patient 82. For example, memory 238 may include a secure digital (SD) card or multimedia card (MMC) that is capable of being removably insertable into WCD system 10 and which can be removed by the medical personnel for retrieval of the collected patient data. In other embodiments, the patient data can be collected and stored in a memory 238 of WCD 10 which can be transmitted to the device 420 of remotely located medical personnel, for example via a radio access network (RAN) 416 coupled to device 420 via a network 418 which may be, for example, the Internet. The device 420 of the medical personnel may comprise a personal computer, a server, a terminal, tablet, and so on that is capable of receiving, storing, accessing, displaying, and/or analyzing the patient data collected by NIBP monitor 150, SpO2 and/or temperature sensor 412, or smartphone 414, and so on.

In some embodiments, NIBP monitor 150 and/or smartphone 414 may include circuitry and/or software to transmit the collected patient data to device 420 via RAN 416. For example, NIBP monitor 150 and/or smartphone 414 can include a cellular modem to communicate with RAN 416 wherein RAN 416 is part of a cellular network, for example operating in accordance with a Third Generation Partnership Project (3GPP) standard. In other embodiments, RAN 416 can be a wireless router that is part of a Wi-Fi or IEEE 802.11x network that is capable of communicating with device 420 via network 418.

In one or more embodiments, an SpO2 sensor such as SpO2 sensor 412 can be powered by a hub portion of the WCD system 10 for example the outside monitoring device 180 of FIG. 1. In some embodiments the outside monitoring device 180 provides connections and circuitry to the sensing electrodes 209 and the sensor port 219 as shown in FIG. 2, wherein at least some of the circuitry of defibrillator 200 may be contained in the outside monitoring device 180 or hub. In those embodiments, an example of which is also shown in and described with respect to FIG. 8 below, sensor port 219 and measurement circuit 220 may be disposed in the hub and can include an analog preamplifier and other analog circuitry to receive analog signals from the patient via the sensing electrodes 209, for example ECG signals. The measurement circuit 220 can include analog-to-digital converts (ADCs) to convert analog signals received via sensing port 219 to digital signals as digital representations of the analog signals which are provided to processor 230. Furthermore, measurement circuit 220 can include an isolation barrier to isolate the analog signals received via sensor port 219 from the digital signals provided to processor 230. Such an isolation barrier may include an opto-isolator or optocoupler and/or an isolation transformer. Thus, the hub can include an isolated side to isolate the ECG signals from the rest of the circuitry of WCD system 10. The SpO2 sensor 412 can connect to the sensor port 219 and be powered from the isolated side of the hub to provide an analog signal connected to an available channel of the measurement circuit 220. For example, measurement circuit 220 can receive four ECG signals from four ECG sensing electrodes 209 and have an additional channel that is used as a common mode signal, referred to as a right-leg drive (RLD). The SpO2 sensor may be connected to the RLD channel of the measurement circuit 220 for the common mode signal that is otherwise not used for recording data. This arrangement would facilitate pulse transit time (PTT) calculations the SpO2 value would be directly correlated to the ECG.

In another embodiment, as shown in FIG. 4 an SpO2 sensor can be incorporated into the alert button 410. In this arrangement, when a reading is needed the patient is prompted to put his or her finger on the SpO2 sensor of the alert button 410. Signals can be digitized at the sensor 412 and transmitted directly to processor 230, which may comprise a system on module (SOM), over a serial communication bus.

In yet another embodiment, an SpO2 sensor can comprise a separate SpO2 and/or temperature sensor 412 that that is cabled from the hub, separate from the alert button 410, in a manner that is similar to the way that the alert button 410 is cabled to the hub but applied to the patient's body in an area that can provide continuous SpO2 and/or temperature measurements. In such embodiments, the additional SpO2 and/or temperature sensors 412 can be powered from the same power supply voltage, for example 3.9 V, that supplies power to the hub. In addition, a communication bus can be multiplexed onto squib fire wires so as not to add additional wires and/or pins to the Therapy Cable and/or Plug of the hub. The measurement circuit 220 includes the hardware capability to measure impedance and respiration in combination with software running on processor 230. In other embodiments, SpO2 and/or temperature sensors 412 can be self-powered, for example from a separate batter, and can communicate with either the external defibrillator 100, sometimes referred to as the monitor, or the outside monitoring device 180, sometimes referred to as the hub, over a lower or medium range wireless communication link such as BLUETOOTH, ZIGBEE, or Wi-Fi, and so on.

The patient data relating to blood pressure, heart rate/pulse, SpO2, and/or temperature can be collected by any one or more of the NIBP monitor 150, SpO2 and/or temperature sensor 412, and/or smartphone 414 can be provided to WCD system 10 analysis that would help medical personnel to understand the patient's health and status during an episode detected by WCD system 10, for example wherein such patient data can be supplemental to the data collected directly by WCD 10 to detect an episode and to make a shock/no-shock decision for the episode. In other embodiments, the collected patient data can be fed into WCD system 10 to provide additional parameters with which an episode can be identified and/or to assist WCD system 10 in making shock/no-shock decisions. The usage of the collected patient data with the monitors and sensors of FIG. 4 is shown in and described with respect to FIG. 6, below. An example embodiment of a wrist worn cuff-less NIBP monitor 150 is shown in and described with respect to FIG. 5, below.

Figure 5:
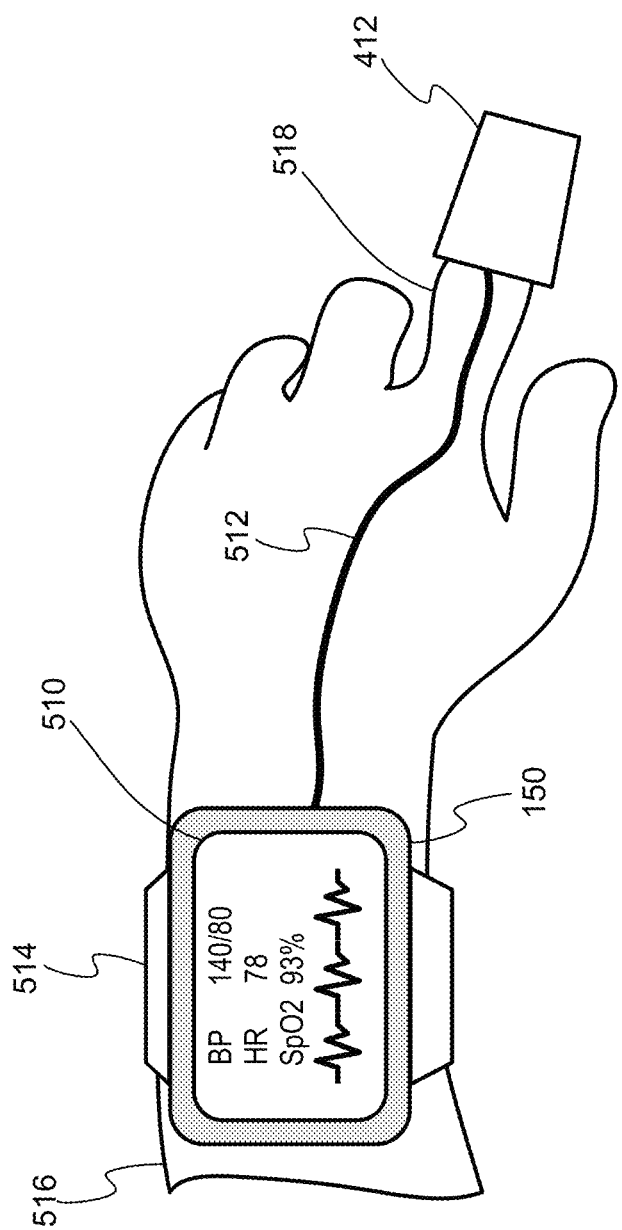
FIG. 5 is a diagram of an example NIBP monitor and SpO2 monitor that are capable of operating with a WCD in accordance with one or more embodiments.

FIG. 5 is a diagram of an example NIBP monitor and SpO2 monitor that are capable of operating with a WCD in accordance with one or more embodiments. The embodiment of NIBP monitor 150 as shown in FIG. 5 shows a wrist worn device that includes a display 510 to display blood pressure, heart rate, and/or SpO2 readings of the patient. The NIBP monitor 150 can be attached to the patient's wrist 516 using a strap 514. In addition, an SpO2 and/or temperature sensor 412 may be attachable to a finger 518 of the patient or may attach to the patient at any suitable location. A cable or wire 512 may be used to connect the SpO2 and/or temperature sensor 412 to the NIBP monitor 150 which can include circuitry to receive and process the signals from the SpO2 and/or temperature sensor 412. In some embodiments, the NIBP monitor 150 can include one or more sensors, processor, input/output circuits, and/or communication modules as discussed herein.

In one or more embodiments, the SpO2 sensor 412 is placed distant from the ECG sensing electrodes 209 and the defibrillation electrodes 204 and 208 of FIG. 2. For example, as shown in FIG. 5, the SpO2 sensor 412 is placed on a patient's finger and away from the other electrodes that are attached to the patient's torso. In particular embodiments, the SpO2 sensor 412 communicates with the WCD system 10 via wireless communication links, for example where the signals provided from the SpO2 sensor 412 to the NIBP monitor 150 is transmitted to the WCD system 10 via a wireless communication link 310 as shown in FIG. 3 or FIG. 4, or wherein the SpO2 sensor 412 is located in the alert button 410 which is typically held in the patient's hand and is generally kept away from the ECG sensing electrodes 209 and the defibrillation electrodes 204 and 208 and are generally located inside and covered by the material of the support structure 170 or garment as shown in FIG. 1 and FIG. 2. In one or more embodiments, NIBP monitor 150 comprises a cuff-less blood pressure device, and in other embodiments NIBP monitor 150 can include a small blood pressure cuff located in or as part of the strap 514, and the scope of the disclosed subject matter is not limited in this respect. Furthermore, in one or more embodiments, NIBP monitor 150 can be configured to utilize pulse transit time (PTT) to obtain continuous blood pressure monitoring, although the scope of the disclosed subject matter is not limited in this respect.

In one or more embodiments, the NIBP monitor 150 can be calibrated to enhance the accuracy of the measurements obtained. For example, NIBP monitor 150 can be calibrated based on one or more external measurements obtained with one or more other NIBP devices. For example, the patient's blood pressure measurement may be obtained using a blood pressure cuff that can provide an electronic blood pressure reading to a smartphone 414 via a wireless communication link. The readings obtained from one or more other devices then can be provided to NIBP monitor 150, and that data can be used to help calibrate the NIBP monitor 150. The data obtained from the other NIBP devices can be provided to NIBP monitor 150 via an electronic connection to the other NIBP devices such as BLUETOOTH, ZIGBEE, or Wi-Fi, or through manual entry such as entering the data via a user interface of NIBP monitor 150, via the web, via an assistant, and so on. The NIBP monitor 150 can have the ability to monitor present and past activity of the patient 82 to determine the best times to collect an accurate NIBP measurement. For example, the NIBP monitor 150 may decide to only take blood pressure measurements after the patient 82 has been inactive for at least five minutes, or at certain times of day that correspond with a resting blood pressure.

NIBP monitor 150 also may assign a reliability score or weighting to measurements based on patient activity to facilitate the analysis of when blood pressure measurements should be obtained. In some embodiments, NIBP monitor 150 may discriminate measurements obtained when the patient has changed from a sitting or lying down position to a standing position. WCD system 10 and/or NIBP monitor 150 can include an accelerometer to detect when the patient 82 has changed positions and to measure the delta in NIBP readings between two or more positions. Furthermore, such patient position based readings can also be used to determine a relative fitness or health measurement of the patient. In one or more embodiments, WCD system 10 can detect patient position and/or movement as described in U.S. application Ser. No. 16/205,861 filed Nov. 30, 2018 and which is incorporated herein by reference in its entirety. Once pertinent readings and measurements have been made, the data may be used to facilitate monitoring of the patient 82 by the WCD system 10 for an episode and/or to facilitate shock or no-shock decisions are shown in and described with respect to FIG. 6, below.

Figure 6:
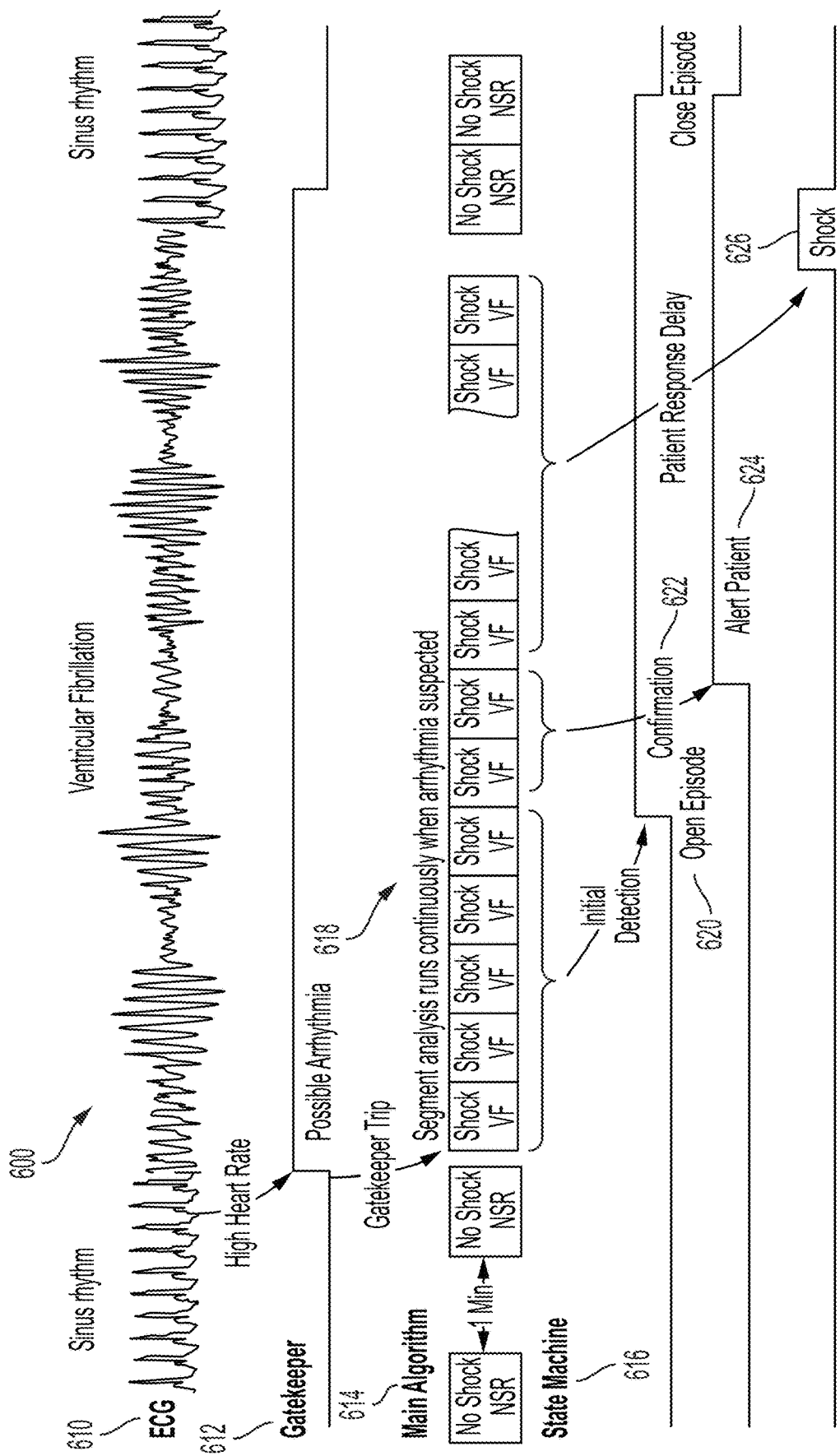
FIG. 6 is a diagram of segment based processing used in a WCD in accordance with one or more embodiments.

FIG. 6 is a diagram of segment based processing used in a WCD in accordance with one or more embodiments. The segment-based processing analysis 600 shown in FIG. 6 is utilized by WCD system 10 to make shock/no-shock decisions based at least in part on successive segments of ECG data. The segments can be 4.8 seconds in duration, although the scope of the disclosed subject matter is not limited in this respect.

The WCD system 10 monitors and analyzes ECG data 610 to make a shock/no-shock decision. A gatekeeper function 612 may be used to provide an early indication that an arrhythmia may be present in the patient 110. An example embodiment of this gatekeeper functionality is disclosed in U.S. application Ser. No. 15/715,500 filed Sep. 26, 2017 which is incorporated herein by reference in its entirety. In some embodiments, if an arrhythmia is suspected with the gatekeeper function 612, then the main rhythm analysis algorithm 614 is triggered to start analyzing successive segments 618 of ECG data, and a shock/no-shock decision is made for each of the individual segments 618. If a string of the segments 618, for example six segments, provide a shock decision, then an episode is opened (Open Episode) 620 in a state machine 616. In some embodiments, this starts an internal storage of ECG information in a memory of the WCD system 10 for later review. After the Open Episode 620, if the shockable rhythm persists for a confirmation period, for example for two or more segments for ventricular fibrillation (VF) or nineteen or more segments for ventricular tachycardia (VT) in some embodiments, then the patient alert sequence (Alert Patient) 624 is initiated. If the patient 82 does not respond within a specified amount of time after initiation of the patient alert sequence, for example after 20 seconds, then a shock (Shock) 626 is delivered to the patient 82.

In some embodiments, measurements from an NIBP monitor 150 can be captured and recorded as part of the episode data. In some cases, a blood pressure measurement obtained with NIBP monitor 150 can open an episode if the measured blood pressure value is below or above predetermined minimum (Min) or maximum (Max) levels. The WCD system 10 can be configured to provide alerts to the patient 82 when measured blood pressure is below or above the predetermined Min/Max levels to provide, for example, a symptom report for example in which a patient can report whether he or she is exercising, experiencing dizziness, shortness of breath, vision problems, migraine, nose bleed, and so on. In some embodiments, the alert may prompt the patient to call 911, notify family members or a physician, check the NIBP monitor 150, and so on. In some embodiments, the alerts can be transmitted to remote parties such as clinicians and family members via the WCD system 10, via the NIBP monitor 150 itself, via a personal communication device such as smartphone 414, and/or via the remote data center or server 420 such as "medical server". In some embodiments, the alert can be transmitted to the patient 82 via the personal communication device in addition to or instead of the WCD monitor component.

In some embodiments, the blood pressure measurement can be used in conjunction with, or as an input to, shock and/or pacing decision algorithms executed by the WCD system 10, for example where a low patient blood pressure can result from the patient being in VF or in bradycardia. In some embodiments, in addition to or instead of being used in therapy decision algorithms, the blood pressure measurement can be used to generate notifications and alerts related to an abnormal blood pressure, or in conjunction with the notifications and alerts provided by the therapy decision algorithms. In still other embodiments, additional sensors may be incorporated in the WCD system 10 to detect other patient parameters that may be used in the decision algorithm such as, for example, heart sound (audio) sensors, SpO2 sensors, Methemoglobin sensors, carbon monoxide sensors, carbon dioxide ($CO_2$) sensors, temperature sensors, impedance, chemical sensors such as perspiration sensors, and so on. The data from these additional sensors optionally can be used in the decision algorithm in some embodiments and/or can be captured for post event or post episode review.

In some embodiments, alerts may be used to prompt the patient 82 to take a blood pressure measurement, for example by having the patient 82 placing his or her finger on an optical NIBP sensor, to implement protocols in which the physician wants to track the patient's blood pressure. In some embodiments, the WCD system 10 can be configured to detect pulseless electrical activity (PEA) using the ECG and NIBP measurements so that the WCD system 10 can alert one or more remote responders and/or prompt bystanders to perform cardiopulmonary resuscitation (CPR) on the patient 82. In some embodiments, the NIBP functionality can be used in providing CPR feedback in real-time or as part of a post event or post episode review. In some embodiments, data from multiple sensors can be aggregated to form vital sign data and provided to the patient, clinician, remote center, and so on. In still other embodiments, the NIBP monitor 150 and/or other sensors can provide vital sign monitoring but does not provide electrical therapy as part of the WCD system 10.

In some embodiments where NIBP monitor 150 comprises an optical NIBP sensor, the blood pressure measurement can be based on pulse transit time (PTT). In cuff-less NIBP sensors based on PTT, the accuracy of the PTT measurements can be increased by incorporating the ECG data in the PTT calculation. In other embodiments, either alone or in combination, other patient signals such as impedance, respiration, acoustic, electro-mechanical, and/or imaging, can be used to enhance the PTT measurement.

In some embodiments, the NIBP measurements, with or without other patient parameters such as heart rate, QRS width, SpO2, temperature, and so on, can be used to calculate a trend, a score, or figure of merit for the current cardiac state of the patient 82. This score can be transmitted to a remote receiver or device 420 as shown in FIG. 4, to a doctor, a family member, a server, and so on, so that a bad trending data or score can alert the doctor or family member or other appropriate personnel to more closely monitor the patient 82, or even bring the patient 82 into a hospital or clinic.

Figure 7:
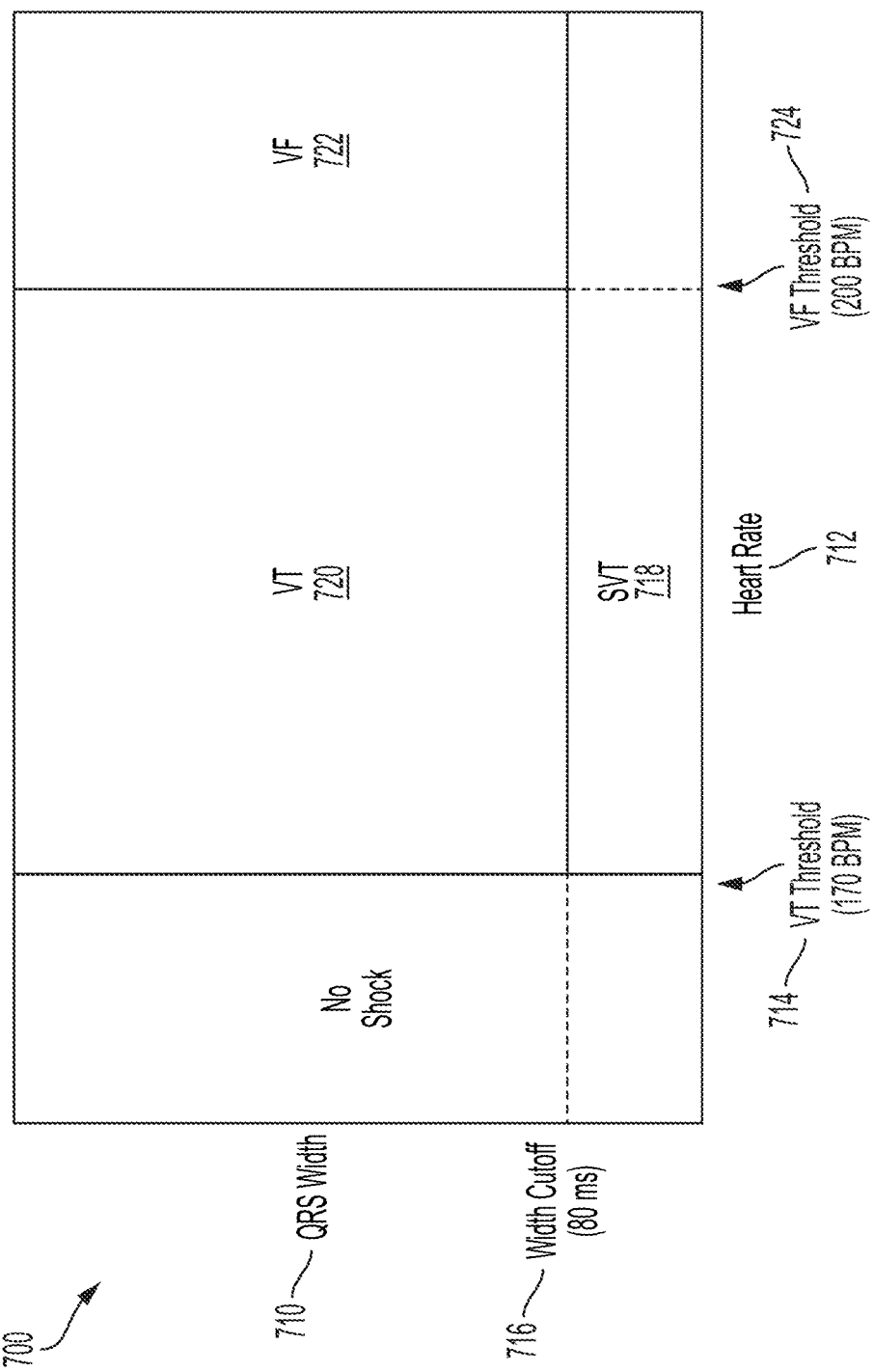
FIG. 7 is a diagram of a shock decision method used in a WCD in accordance with one or more embodiments.

FIG. 7 is a diagram of a shock decision method used in a WCD in accordance with one or more embodiments. In one or more embodiments, WCD system 10 can utilize a rhythm analysis algorithm (RAA) to make shock/no-shock decisions based on the patient's heart rate and QRS width according to graph 700. QRS width 710 is shown on the vertical axis, and heart rate 712 is shown on the horizontal axis. As shown in FIG. 7, all rhythms with a heart rate below the ventricular tachycardia (VT) threshold 714, for example 170 beats per minute (BPM), can be considered non-shockable. All rhythms below the QRS width cutoff 716, for example 80 milliseconds (ms), can be considered non-shockable as well. Above the VT threshold 714, narrow rhythms are classified as super ventricular tachycardia (SVT) 718. Fast, wide rhythms are classified either as ventricular tachycardia (VT) 720 or ventricular fibrillation (VF) 722, depending on the heart rate. For example, in some embodiments heart rate above a VF threshold 724 of 200 BPM with a QRS width above the QRS width cutoff threshold 716 would be classified as VF 722. Both VT 720 and VF 722 are considered shockable conditions.

In one or more embodiments, an NIBP measurement obtained by NIBP monitor 150 can be incorporated into the RAA algorithm for example as illustrated in FIG. 7. The goal of the WCD system 10 is to treat people with pulseless VT/VF. Current WCDs (and ICDs) are guessing whether the patient has a pulse or not based on the heart rate. It may be possible to avoid unnecessary shocks and possibly increase patient survival if the WCD system 10 truly knew whether the patient 82 had a pulse or not. In some embodiments, NIBP information obtained by NIBP monitor 150 can be utilized to modify the shock criteria to deliver a shock only when the patient 82 has a high heart rate and very low blood pressure. The blood pressure threshold can be set the same way the heart rate threshold is set as shown in FIG. 7 for a particular patient.

In some embodiments, the RAA algorithm analyzes ECG data in 4.8 second segments, for example as shown in FIG. 6. For each segment, the heart rate, R-wave width, and QRS organization are calculated. These parameters are used to determine ECG rhythm and to decide whether a shock is appropriate. If a number of segments successively have a "shock" result, the WCD system 10 will start to alarm. If the patient doesn't respond to the alarm, then a shock is delivered. In embodiments described herein where the WCD system 10 can measure blood pressure using NIBP monitor 150, the WCD system 10 can record a blood pressure measurement corresponding each segment. Such an arrangement can allow the WCD system 10 to discriminate perfusing VT from non-perfusing VT. The WCD system 10 would then only alarm and shock for non-perfusing VT and VF.

In some embodiments, blood pressure can be used as an "SVT discriminator" in the VT zone 720. Patients with heart rates below the VT threshold 714 would never be shocked, and heart rates above the VF threshold 724 would be shocked regardless of the blood pressure, but heart rates in the VT zone 720 would only be shocked if the blood pressure as obtained from NIBP monitor 150 was below a threshold value. This analysis can be done independently from R-wave width, that is it can be applied in shock non-perfusing SVT zone 718 as well as in the VT zone 734, or the WCD system 10 can only shock non-perfusing rhythms with wide complexes.

In other embodiments, blood pressure readings obtained with NIBP monitor 150 can be used to help detect low-rate polymorphic ventricular tachycardia (PVT) below the VT threshold 714. PVT refers to a rapid ventricular rhythm with a continuously varying QRS complex morphology wherein the QRS complex varies from beat to beat. PVT can be fatal, even if the heart rate is below the rate thresholds shown in FIG. 7. In some embodiments, the ECG analysis algorithm used by WCD system 10 can detect some low-rate PVT using the heart rate, R-wave width, and QRS organization. Some physicians, however, may fear that patients will be inappropriately shocked if there is a possibility of shocking someone below the VT threshold 714. If the WCD system 10 was able to determine that the patient 82 had a disorganized ventricular rhythm that met the predefined rate criteria and had an extremely low blood pressure, WCD system 10 can have extra confidence that shocking PVT is the right thing to do for the patient 82, which can save lives.

In further embodiments, blood pressure readings obtained with NIBP monitor 150 can be used to enhance treatment of wide-complex rhythms in the VF zone 722. The WCD system 10 can give an alarm and shock for these rhythms, but the WCD system 10 does not necessarily need to shock quickly. If the patient 82 has perfusion, it may be preferable to shock more slowly to allow the rhythm time to self-terminate.

In other embodiments, blood pressure readings obtained with NIBP monitor 150 can be used to eliminate the use heart rate zones altogether. If the patient 82 is non-perfusing as detected by NIBP monitor 150, then everything above a minimum rate cutoff, for example 135 beats per minute (BPM) can be shocked. Alternatively, everything with wide complexes above a minimum rate cutoff can be shocked.

In other embodiments, VF detection accuracy can be enhanced with NIBP monitor 150 by looking for a sudden loss of blood pressure that is coincident with an increased heart rate, wider R-wave width, and disorganized rhythm. It is possible that the WCD system 10 could look for such a combination to accelerate therapy to treat VF more quickly without risking unnecessary shocks. In some embodiments, NIBP monitor 150 can be used to obtain a heart rate value independently from the heart rate value obtained via the ECG of WCD system 10. Using NIBP monitor 150 in such a manner as an independent source of heart rate data can be used to help with heart rate noise discrimination in the ECG data.

In addition to enhancing VT/VF detection and treatment, a blood pressure measurement obtained by NIBP monitor 150 can enhance asystole/bradycardia detection. If the ECG says that the patient 82 is in asystole but the NIBP monitor 150 detects a reasonable blood pressure, then obviously something isn't right. Furthermore, using NIBP monitor 150 to obtain a blood pressure measurement can also be useful for detecting heart failure decompensation which can be detected by WCD system 10.

Figure 8:
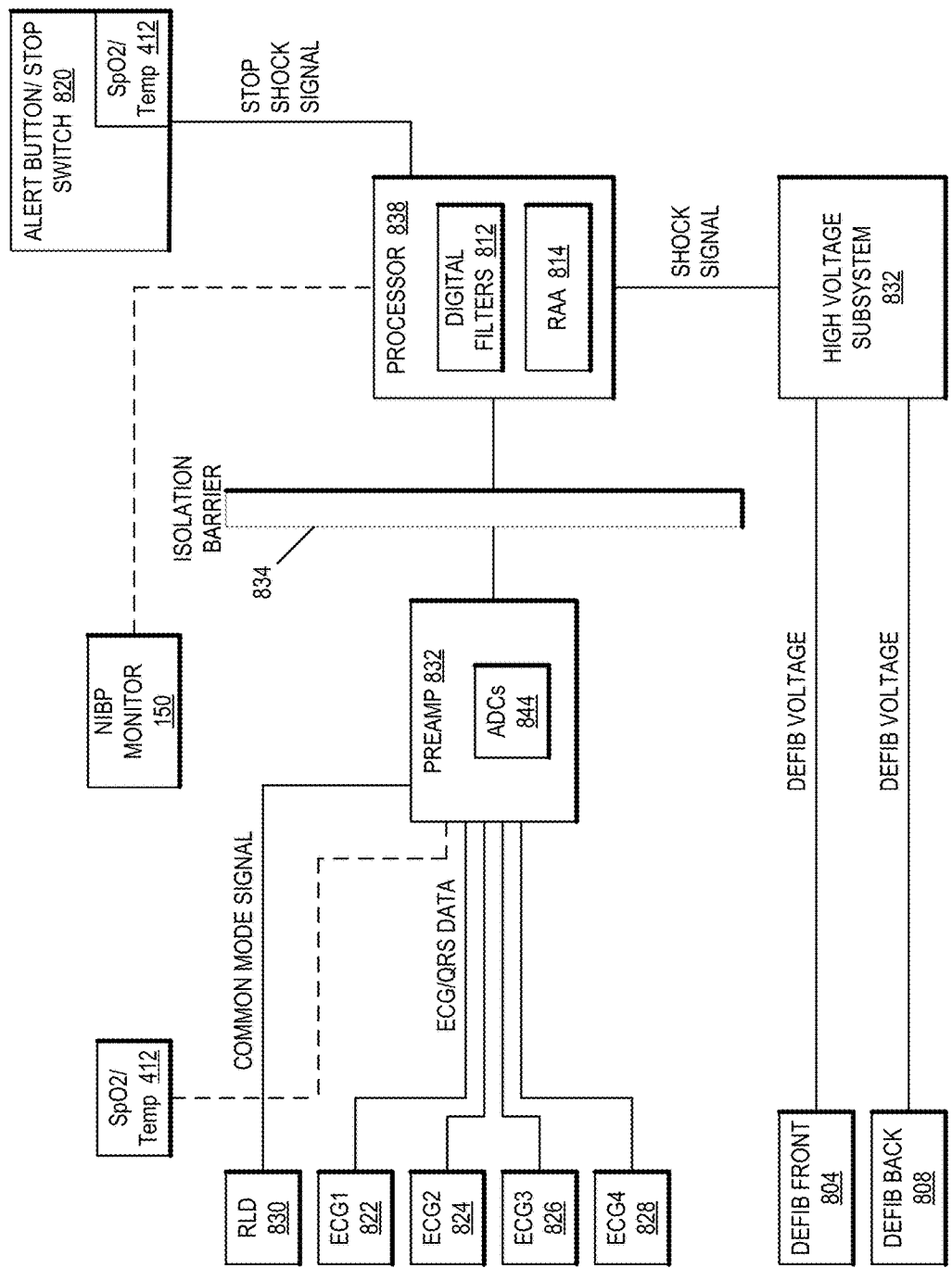
FIG. 8 is a diagram of a WCD that can obtain patient parameters from an NIBP monitor and an SpO2 monitor in accordance with one or more embodiments.

Referring now to FIG. 8, a diagram of a wearable system that can obtain patient parameters from an NIBP monitor and an SpO2 monitor in accordance with one or more embodiments will be discussed. The wearable system 800 of FIG. 8 can comprise a WCD system 10 that incorporates one or more of the features discussed herein to enhance ECG and QRS complex signal data detection along with heart rate data detection, NIBP monitor 150 and SpO2 and/or temperature sensor 412. The ECG electrodes, ECG1 822, ECG2 824, ECG3 826, and ECG4 828, can comprise silver or silver plated copper electrodes that "dry" attach to the skin of the patient 82. The ECG electrodes provide ECG/QRS data to preamplifier 832. The preamplifier 832 may have a wide dynamic range at its input, for example +/−1.1 V which is much larger than the amplitude of the ECG signals which are about 1 mV. The preamplifier 832 includes analog-to-digital converters (ADCs) 844 to convert the ECG signals into a digital format. A right-leg drive (RLD) electrode 830 is used to provide a common mode signal so that the ECG signal from the ECG electrodes may be provided to preamplifier 832 as differential signals. The digital ECG signals are provided from the preamplifier 832 eventually to the main processor 838 via an isolation barrier 834 which operates to electrically isolate the preamplifier 832 and the ECG signals from the rest of the circuity of WCD system 10.

The processor 838 processes the digital ECG/QRS data received from the preamplifier 832 with one or more digital filters 812. Since the preamplifier 832 has a wide dynamic range that is much wider than the amplitude range of the ECG signals, digital filters 812 may be utilized to process the ECG/QRS data without concern for clipping the incoming signals. One of the digital filters 812 may include a matched filter to facilitate identification of QRS pulses in the incoming data stream. The wide dynamic range of the preamplifier 832 allows at least most of the ECG filtering to happen in software without the signal being clipped. Digital filters 812 can be very effective at removing artifacts from the ECG/QRS data and may contribute to the enhanced false positive performance, that is a lower false positive rate, of the WCD system 10 according to embodiments as described herein.

The processor 838 can apply the rhythm analysis algorithm (RAA) 814 using QRS width information and heart rate data extracted from the digital ECG data using the segment-based processing analysis 600 of FIG. 6 and the QRS width versus heart rate graph 700 of FIG. 7 to make a shock or no-shock determination. The RAA 814 receives the digitized ECG signal and calculates the heart rate and QRS width for each segment. The digitized ECG signal is passed over the isolation barrier 834, and the heart rate is derived from the digitized ECG signal. The heart rate and QRS width are used for making a shock/no-shock decision for each segment, which then can lead to an alarm and a shock. In the event a shockable event is identified, the processor 838 will open a tachycardia episode to start the shock process. Unless the patient 82 provides a patient response using the alert button/stop switch 820 or other user interface of the WCD system 10 to send a stop shock signal to the processor 838 to intervene before the shock is applied, the processor 838 can send a shock signal to the high voltage subsystem 832 which will apply a defibrillation voltage across the defib front electrode 804 and the defib back electrode 808 to apply one or more therapeutic shocks until there is no longer any shockable event (VT or VF) or until the energy in the battery of the high voltage subsystem 832 is depleted.

In one or more embodiments of the WCD system 10, the digital filters 812 coupled with the wide dynamic range of the preamplifier 832 may allow analysis of signals that otherwise would be clipped in systems with a more limited dynamic range. In addition, the matched filter of the digital filters 812 preferentially highlights complexes similar to the patient's normal rhythm. As a result, artifacts that otherwise may be difficult to discriminate using other methods may be significantly attenuated by the matched filter.

In accordance with one or more embodiments, SpO2 and/or temperature sensor 412 can be coupled to the preamp 832 via the common mode signal line as discussed herein. Alternatively, the SpO2 and/or temperature sensor can be integrated with the alert button/stop switch 820 and coupled to processor 838. The NIBP monitor 150 can be coupled to the processor 838 via a wired link or a wireless communication link as discussed herein. In some embodiments, patient impedance measurements may be obtained between any two or more of the ECG electrodes, for example to determine a patient's respiration. In some embodiments, the wearable system 800 can comprise a WCD system 10 as discussed herein. In other embodiments, the wearable system 800 can comprise a wearable patient monitoring system that is capable of collecting one or more patient parameters that can be stored in a memory for future review and analysis, and/or to provide one or more warnings to a patient that one or more patient parameters are outside a normal or predetermined range when the patient is wearing the patient monitoring system, for example to allow the patient to cease a present activity that may be causing an atypical patient parameter or to otherwise seek assistance or medical help. In such embodiments, wearable system does not necessarily include structure to provide defibrillation therapy to the patient. It should be noted, however, that these are merely example implementations of wearable system 800, and the scope of the disclosed subject matter is not limited in this respect.

Other embodiments include combinations and sub-combinations of features described or shown in the drawings herein, including for example, embodiments that are equivalent to: providing or applying a feature in a different order than in a described embodiment, extracting an individual feature from one embodiment and inserting such feature into another embodiment; removing one or more features from an embodiment; or both removing one or more features from an embodiment and adding one or more features extracted from one or more other embodiments, while providing the advantages of the features incorporated in such combinations and sub-combinations. As used herein, feature or features can refer to the structures and/or functions of an apparatus, article of manufacture or system, and/or the operations, acts, or modalities of a method.

The following examples may be implemented in accordance with one or more embodiments. In example one, a wearable cardioverter defibrillator (WCD) system comprises a plurality of patient parameter electrodes and a plurality of defibrillator electrodes to contact a patient's skin when the WCD is delivering therapy to the patient, a processor to receive one or more patient parameters from the one or more patient parameter electrodes, an energy storage device to store a charge to provide electrical therapy to the patient via the plurality of defibrillator electrodes, and a non-invasive blood pressure (NIBP) monitor to obtain a blood pressure measurement of the patient and to provide the blood pressure measurement to the processor. The processor is to determine whether to provide electrical therapy to the patient based on the one or more patient parameters during an episode, and to obtain the blood pressure measurement from the NIBP monitor during the episode. In example two, the processor is to generate an alert when the blood pressure measurement has a value that is below a minimum value or above a maximum value. In example three, the processor is to generate a prompt for the patient to obtain a blood pressure measurement. In example four, the processor is to use the blood pressure measurement during the episode in combination with the one or more patient parameters to determine whether to provide electrical therapy to the patient. In example five, the NIBP monitor is disposed in an alert button coupled to the WCD system. In example six, the NIBP monitor is coupled to one or more of the patient parameter electrodes. In example seven, the NIBP monitor is attachable to an arm, a leg, a wrist, or an ankle of the patient. In example eight, the NIBP monitor is attachable to a body of the patient. In example nine, the NIBP monitor is disposed in a smartphone or a wearable device that is capable of transmitting the blood pressure measurement to processor via a wired or a wireless communication link. In example ten, the NIBP monitor comprises an SpO2 sensor or a temperature sensor, or a combination thereof.

In example eleven, a wearable cardioverter defibrillator (WCD) system comprises a plurality of patient parameter electrodes and a plurality of defibrillator electrodes to contact a patient's skin when the WCD is delivering therapy to the patient, a processor to receive one or more patient parameters from the one or more patient parameter electrodes, wherein the one or more patient parameters includes electrocardiogram (ECG) data, an energy storage device to store a charge to provide electrical therapy to the patient via the plurality of defibrillator electrodes, and a non-invasive blood pressure (NIBP) monitor to obtain a blood pressure measurement of the patient and to provide the blood pressure measurement to the processor. The processor is to determine whether to provide electrical therapy to the patient based on the one or more patient parameters and the blood pressure measurement during an episode. In example twelve, the electrical therapy is applied to the patient when the processor determines that the patient has a heart rate above a heart rate threshold and a blood pressure below a blood pressure threshold. In example thirteen, the processor is to analyze the ECG data in segments of ECG data and to obtain a blood pressure measurement for each of the segments of ECG data, wherein a determination is made to provide electrical therapy to the patient when a string of a predetermined number of segments indicate a shock decision should be made and ventricular tachycardia (VT) criterion is met and the patient is in an non-perfusing state. In example fourteen, a determination is not made to provide electrical therapy to the patient when the VT criterion is met and the patient is perfusing. In example fifteen, a determination is made to provide electrical therapy to the patient when a super ventricular tachycardia (SVT) criterion is met and the patient is non-perfusing. In example sixteen, a determination is made to provide electrical therapy to the patient when the processor determines that the patient has a disorganized ventricular rhythm and has a blood pressure reading below a predetermined threshold. In example seventeen, a determination is made to provide electrical therapy to the patient when the ECG data indicates the patient is in the ventricular fibrillation (VF) zone, and wherein time between shocks is increased to allow a heart rhythm to self-terminate when the patient is perfusing. In example eighteen, a determination is made to provide electrical therapy to the patient when the patient's heart rate is above a minimum threshold and the patient is non-perfusing, or when the patient's QRS complex width is above a minimum threshold and the patient is non-perfusing. In example nineteen, a determination is made to provide electrical therapy to the patient when a sudden drop in blood pressure occurs coincident with an increased heart rate, an increase in R-wave width, and a disorganized heart rhythm. In example twenty, the NIBP monitor is to obtain a heart rate value independent from the ECG data.

In example twenty-one, wearable patient monitoring system comprises a support structure configured to be worn by a patient, a plurality of patient sensors including a non-invasive blood pressure (NIBP) monitor to be coupled to the patient when the patient is wearing the support structure, and a processor coupled to the plurality of patient sensors to collect one or more patient parameters, and a memory coupled to the processor to store the one or more patient parameters including one or more blood pressure readings obtained with the NIBP monitor. In example twenty-two, the plurality of patient sensors includes an ECG sensor to obtain patient ECG data when the patient is wearing the support structure. In example twenty-three, the plurality of patient sensors includes a temperature sensor to obtain a patient temperature reading when the patient is wearing the support structure. In example twenty-four, the plurality of patient sensors includes a patient impedance sensor to obtain a patient impedance reading when the patient is wearing the support structure. In example twenty-five, the patient impedance reading is used to determine patient respiration information.

Although the claimed subject matter has been described with a certain degree of particularity, it should be recognized that elements thereof may be altered by persons skilled in the art without departing from the spirit and/or scope of claimed subject matter. It is believed that the subject matter pertaining to wearable cardioverter defibrillator with a non-invasive blood pressure monitor and many of its attendant utilities will be understood by the foregoing description, and it will be apparent that various changes may be made in the form, construction and/or arrangement of the components thereof without departing from the scope and/or spirit of the claimed subject matter or without sacrificing all of its material advantages, the form herein before described being merely an explanatory embodiment thereof, and/or further without providing substantial change thereto. It is the intention of the claims to encompass and/or include such changes.

What is claimed is:

1. A wearable patient monitoring system, comprising:
   a support structure configured to be worn by a patient;
   a housing;
   a plurality of patient sensors including a non-invasive blood pressure (NIBP) monitor to be coupled to the patient when the patient is wearing the support structure, wherein the NIBP monitor is configured obtain a blood pressure measurement based on a pulse transit time (PTT) measurement, and wherein the plurality of patient sensors includes an ECG sensor to obtain patient ECG data when the patient is wearing the support structure;
   one or more processors in the housing and coupled to the plurality of patient sensors to collect one or more patient parameters, wherein the one or more processors are configured to receive the patient ECG data from the ECG sensor and the blood pressure measurement from the NIBP monitor to determine the PTT, wherein the patient ECG data is used to increase accuracy of the PTT measurement to generate an enhanced accuracy blood pressure measurement; and
   a memory coupled to the one or more processors to store the one or more patient parameters including one or more blood pressure readings obtained with the NIBP monitor; and
   wherein the one or more processors are configured to determine whether the patient is experiencing ventricular tachycardia (VT) based at least in part on the patient ECG data, and to determine whether the VT is perfusing VT or non-perfusing VT based at least in part on the enhanced accuracy blood pressure measurement.

2. The wearable patient monitoring system of claim 1, wherein the plurality of patient sensors includes a temperature sensor to obtain a patient temperature reading when the patient is wearing the support structure.

3. The wearable patient monitoring system of claim 1, wherein the plurality of patient sensors includes a patient impedance sensor to obtain a patient impedance reading when the patient is wearing the support structure, wherein the patient impedance reading is used to determine patient respiration information.

4. The wearable patient monitoring system of claim 1, wherein at least one of the one or more processors is configured to generate an alert when the enhanced accuracy blood pressure measurement has a value that is below a minimum value or above a maximum value.

5. The wearable patient monitoring system of claim 1, wherein at least one of the one or more processors is configured to generate a prompt for the patient to obtain a blood pressure measurement.

6. The wearable patient monitoring system of claim 1, wherein:
the one or more processors are configured to use the enhanced accuracy blood pressure measurement during an episode in combination with the one or more patient parameters to determine whether the patient requires electrical therapy.

7. The wearable patient monitoring system of claim 1, wherein:
the NIBP monitor is disposed in a button coupled to the wearable patient monitoring system.

8. The wearable patient monitoring system of claim 1, wherein:
the NIBP monitor is coupled to the ECG sensor.

9. The wearable patient monitoring system of claim 1, wherein the NIBP monitor is attachable to an arm, a leg, a wrist, or an ankle of the patient, or at another location on the patient's body.

10. The wearable patient monitoring system of claim 1, wherein the NIBP monitor is disposed in a smartphone or a wearable device that is capable of transmitting the enhanced accuracy blood pressure measurement to processor via a wired or a wireless communication link.

11. The wearable patient monitoring system of claim 1, wherein the NIBP monitor comprises an SpO2 sensor or a temperature sensor, or a combination thereof.

12. The wearable patient monitoring system of claim 1, wherein:
the one or more processors are configured to determine when the patient has a heart rate above a heart rate threshold and a blood pressure below a blood pressure threshold.

13. The wearable patient monitoring system of claim 1, wherein:
the one or more processors are configured to analyze the patient ECG data in segments of patient ECG data and to obtain a blood pressure measurement for one or more of the segments of patient ECG data; and
wherein the one or more processors are configured to determine when a string of a predetermined number of segments indicate a ventricular tachycardia (VT) criterion is met and the patient is in a non-perfusing state.

14. The wearable patient monitoring system of claim 13, wherein:
the one or more processors are configured to determine when the VT criterion is met and the patient is perfusing, and when a super ventricular tachycardia (SVT) criterion is met and the patient is non-perfusing.

15. The wearable patient monitoring system of claim 1, wherein:
the one or more processors are configured to determined when the patient has a disorganized ventricular rhythm and has a blood pressure reading below a predetermined threshold, and when the patient ECG data indicates the patient is in a ventricular fibrillation (VF) zone.

16. The wearable patient monitoring system of claim 1, wherein:
the one or more processors are configured to determine when the patient's heart rate is above a minimum threshold and the patient is non-perfusing, when the patient's QRS complex width is above a minimum threshold and the patient is non-perfusing, and when a sudden drop in blood pressure occurs coincident with an increased heart rate, an increase in R-wave width, or a disorganized heart rhythm.

17. The wearable patient monitoring system of claim 1, wherein the NIBP monitor is configured to obtain a heart rate value independent from the patient ECG data.

18. A wearable patient monitoring system, comprising:
a support structure configured to be worn by a patient;
a plurality of patient sensors including a single non-invasive blood pressure (NIBP) monitor to be coupled to the patient when the patient is wearing the support structure, wherein the NIBP monitor is configured obtain a blood pressure measurement based on a pulse transit time (PTT) measurement, and wherein the plurality of patient sensors includes an ECG sensor to obtain patient ECG data when the patient is wearing the support structure;
one or more processors coupled to the plurality of patient sensors to collect one or more patient parameters, wherein the one or more processors are configured to receive the blood pressure measurement from the single NIBP monitor to determine the PTT, wherein the patient ECG data is used to increase accuracy of the PTT measurement to generate an enhanced accuracy blood pressure measurement; and
a memory coupled to the one or more processors to store the one or more patient parameters including one or more blood pressure readings obtained with the NIBP monitor; and
wherein the one or more processors are configured to determine whether the patient is experiencing ventricular tachycardia (VT) based at least in part on the patient ECG data, and to determine whether the VT is perfusing VT or non-perfusing VT based at least in part on the enhanced accuracy blood pressure measurement.

19. The wearable patient monitoring system of claim 18, wherein:
the one or more processors are configured to use the enhanced accuracy blood pressure measurement during an episode in combination with the one or more patient parameters to determine whether the patient requires electrical therapy.

* * * * *